United States Patent
Imai

(10) Patent No.: US 10,190,992 B2
(45) Date of Patent: Jan. 29, 2019

(54) STRUCTURE STATUS DETERMINATION DEVICE, STATUS DETERMINATION SYSTEM, AND STATUS DETERMINATION METHOD

(71) Applicant: NEC Corporation, Minato-ku, Tokyo (JP)

(72) Inventor: Hiroshi Imai, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 15/555,154

(22) PCT Filed: Mar. 14, 2016

(86) PCT No.: PCT/JP2016/001421
§ 371 (c)(1),
(2) Date: Sep. 1, 2017

(87) PCT Pub. No.: WO2016/152075
PCT Pub. Date: Sep. 29, 2016

(65) Prior Publication Data
US 2018/0052117 A1    Feb. 22, 2018

(30) Foreign Application Priority Data
Mar. 20, 2015 (JP) .................. 2015-057047

(51) Int. Cl.
*G01B 11/30* (2006.01)
*G01N 21/88* (2006.01)
*G01M 5/00* (2006.01)

(52) U.S. Cl.
CPC ......... *G01N 21/8851* (2013.01); *G01B 11/30* (2013.01); *G01M 5/0033* (2013.01); *G01M 5/0075* (2013.01); *G01M 5/0091* (2013.01); *G01N 21/88* (2013.01); *G01N 2021/8864* (2013.01); *G01N 2021/8896* (2013.01)

(58) Field of Classification Search
CPC ............... G01N 21/8851; G01N 21/88; G01N 2021/8864; G01N 2021/8896;
(Continued)

(56) References Cited

U.S. PATENT DOCUMENTS

2002/0154811 A1    10/2002    Katsuta et al.
2006/0098861 A1    5/2006    See et al.
(Continued)

FOREIGN PATENT DOCUMENTS

JP    S62-150111 A    7/1987
JP    2002-236100 A    8/2002
(Continued)

OTHER PUBLICATIONS

Written Opinion of International Search Authority dated Jun. 7, 2016, in counterpart international application No. PCT/JP2016/001421.
(Continued)

*Primary Examiner* — Samir A Ahmed

(57) ABSTRACT

The purpose of the present invention is to accurately detect structures from a remote location without contact while distinguishing between defects such as cracking, separation, and internal cavities. This status determination device includes: a displacement calculation unit that calculates a two-dimensional spatial distribution of displacement in time-series images, said time-series images being taken before and after a load is applied to a surface of a structure; a correction amount calculation unit that calculates a correction amount from the two-dimensional spatial distribution of displacement in the time-series images, said correction amount being based on the amount of movement of the structure surface in the normal direction as induced by said loading; a displacement correction unit that subtracts the correction amount from the two-dimensional spatial distri- (Continued)

bution of displacement in the time-series images, and extracts a two-dimensional spatial distribution of displacement of the structure surface; and an abnormality determination unit for identifying defects in the structure on the basis of a comparison of the two-dimensional spatial distribution of displacement of the structure surface and a pre-prepared spatial distribution of displacement.

10 Claims, 30 Drawing Sheets

(58) Field of Classification Search
CPC ............ G01M 5/0091; G01M 5/0075; G01M 5/0033; G01B 11/30
See application file for complete search history.

(56) References Cited

U.S. PATENT DOCUMENTS

2008/0160431 A1* 7/2008 Scott ...................... B82Y 10/00
430/5

2015/0215584 A1* 7/2015 Tapia ................. G01N 21/8851
348/125

FOREIGN PATENT DOCUMENTS

| | | |
|---|---|---|
| JP | 2003-035528 A | 2/2003 |
| JP | 2004-347585 A | 12/2004 |
| JP | 2005-533320 A | 11/2005 |
| JP | 2006-343160 A | 12/2006 |
| JP | 2007-071793 A | 3/2007 |
| JP | 2008-232998 A | 10/2008 |
| JP | 2012-132786 A | 7/2012 |

OTHER PUBLICATIONS

International Search Report dated Jun. 7, 2016, in counterpart international application No. PCT/JP2016/001421.

Zhen Wang et al., "Crack-opening displacement estimation method based on sequence of motion vector field images for civil infrastructure deterioration inspection", Image Media Processing Symposium (PCSJ/IMPS2014), Jan. 1, 2017, The Institute of Electronics, Information and Communication Engineers, Nov. 12, 2014, total 2 pages.

* cited by examiner

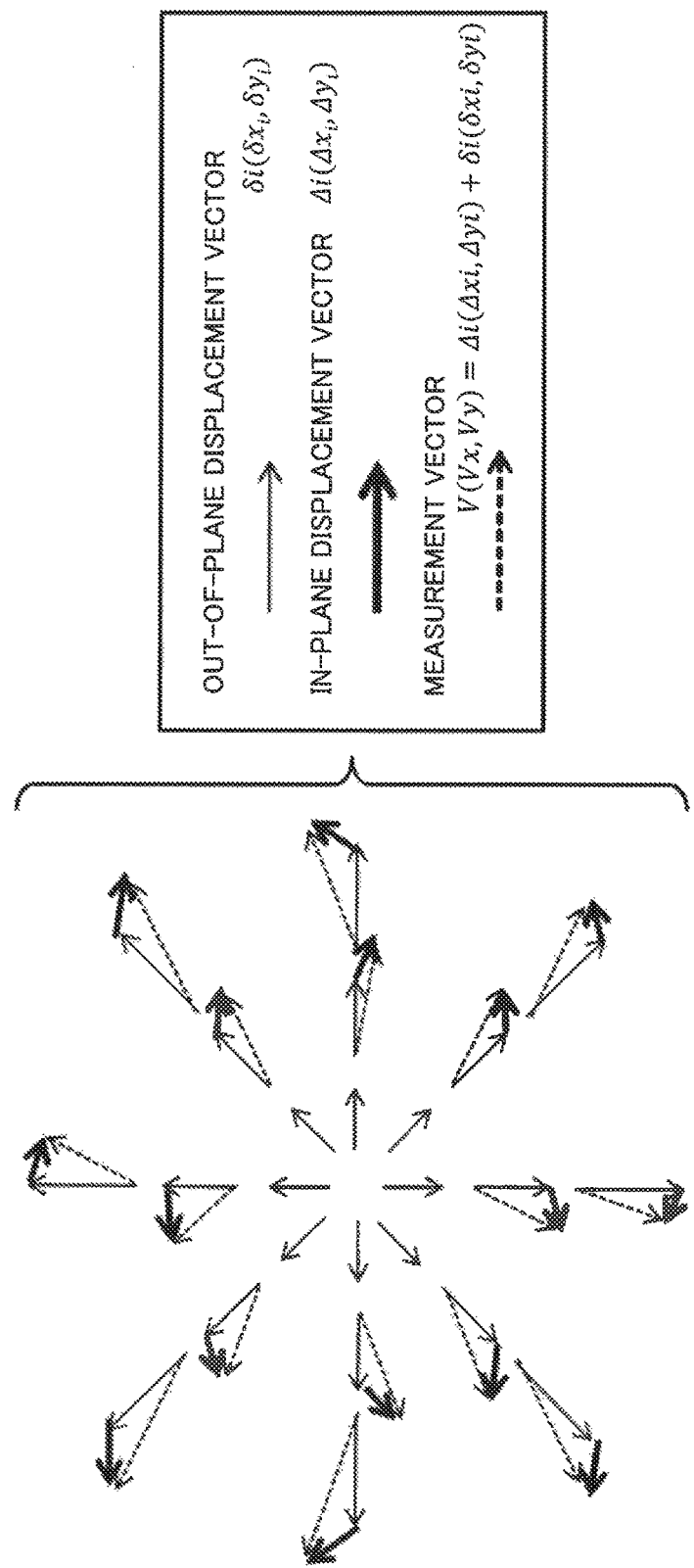

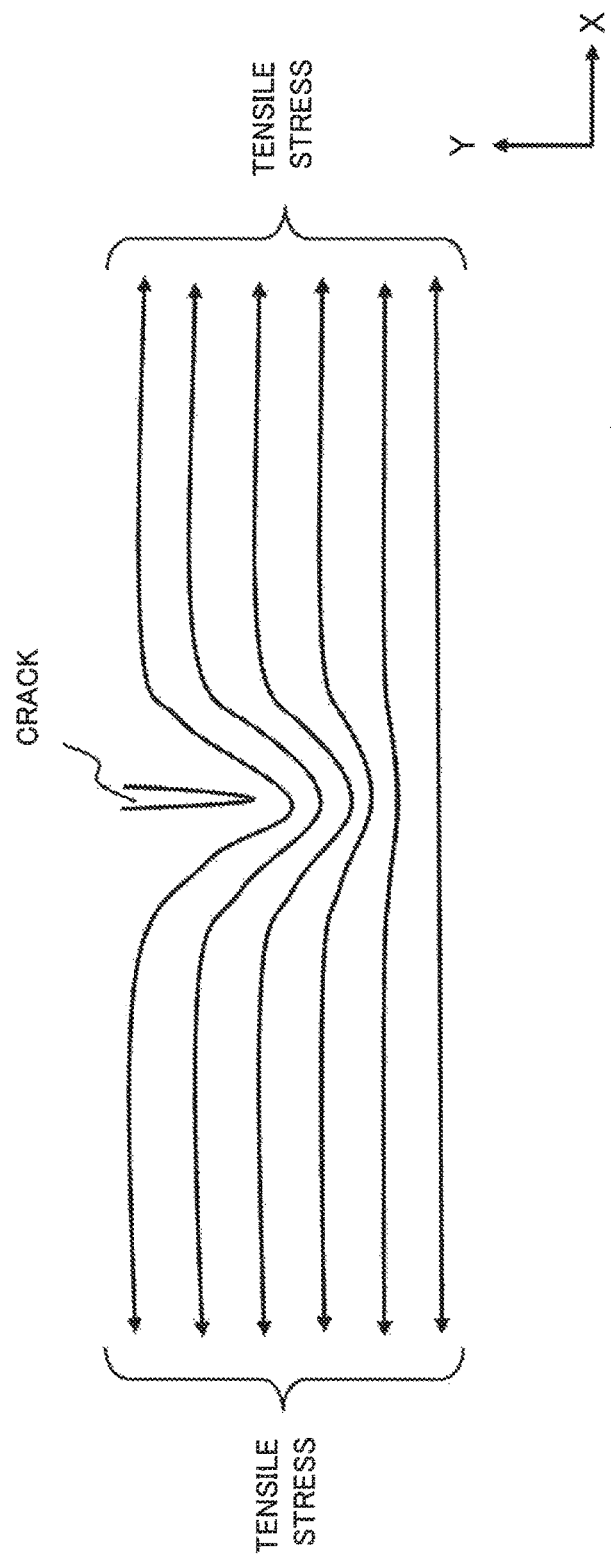

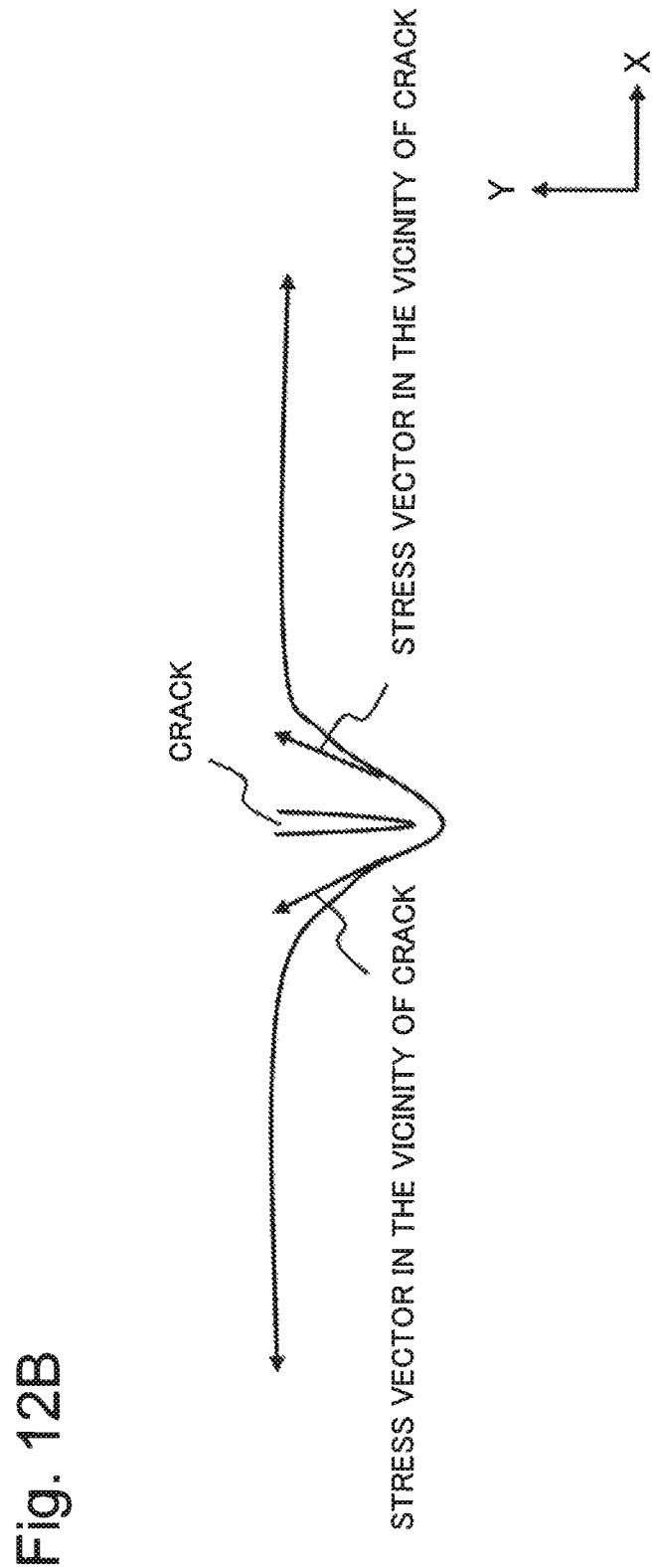

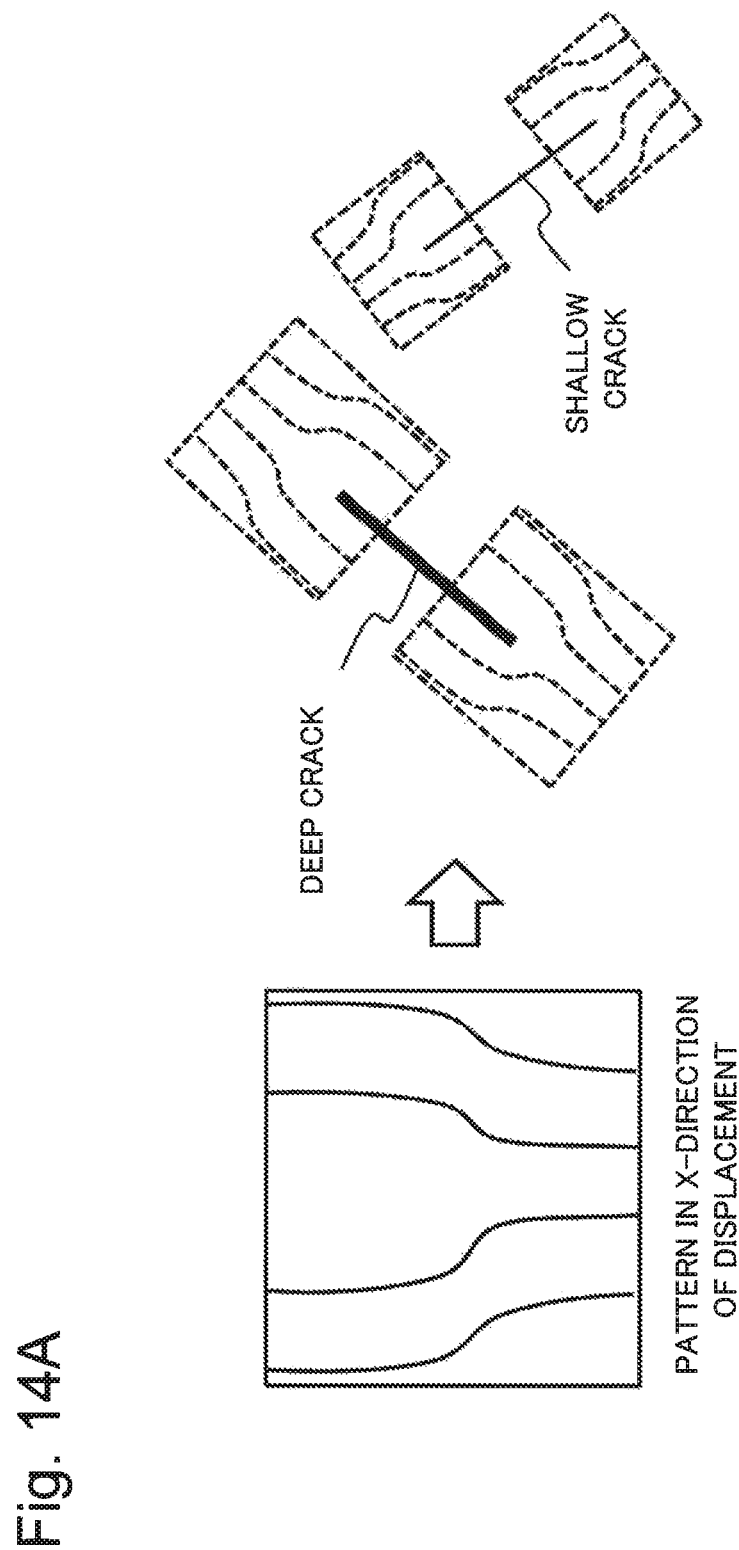

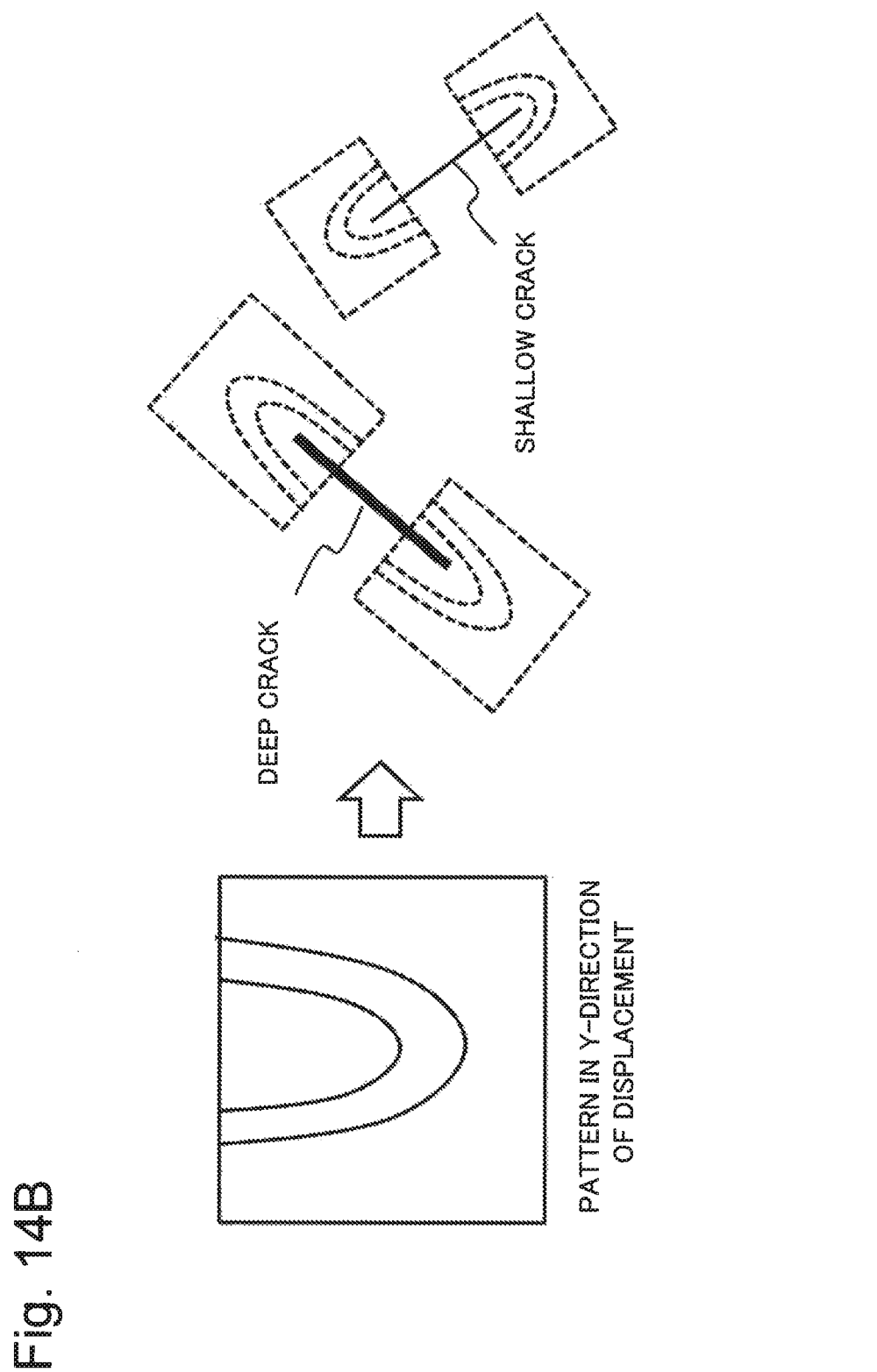

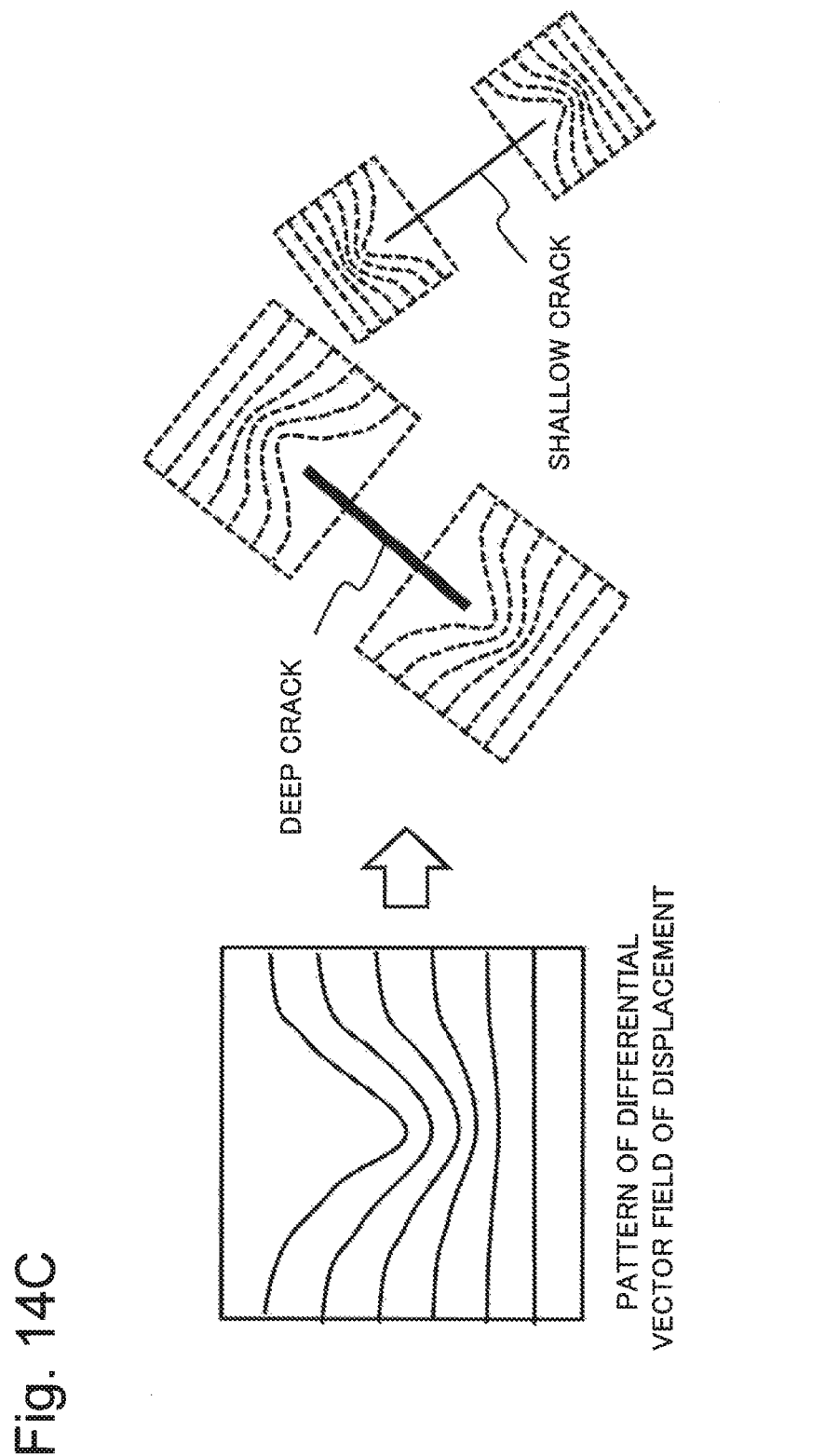

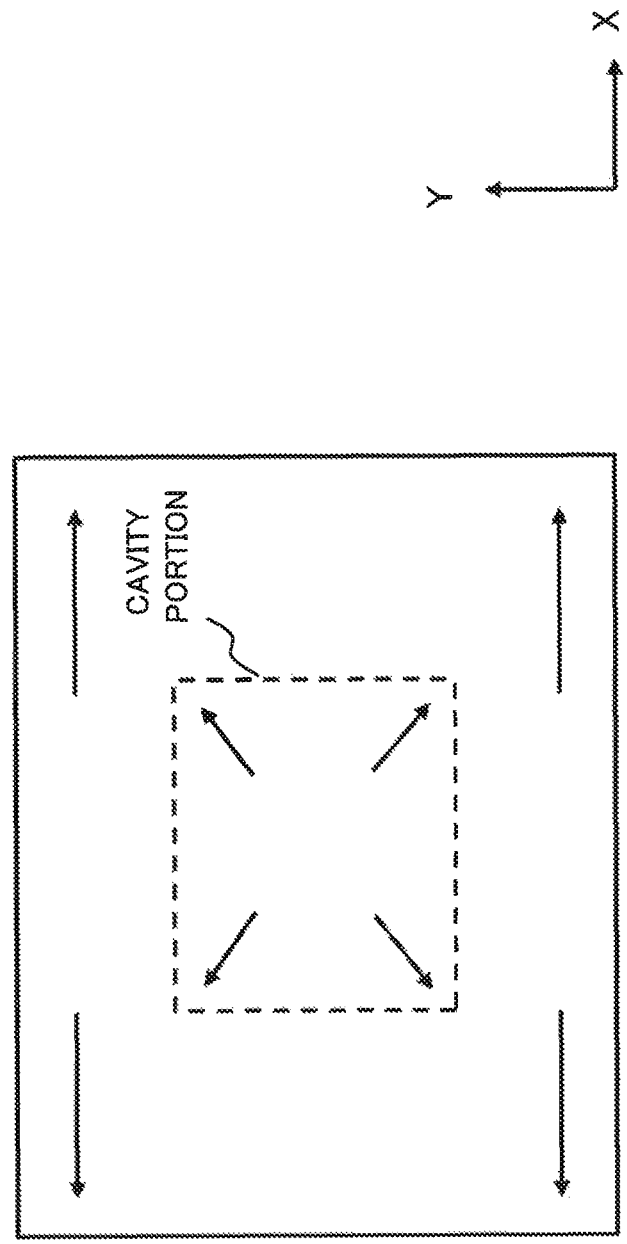

STRUCTURE STATUS DETERMINATION DEVICE, STATUS DETERMINATION SYSTEM, AND STATUS DETERMINATION METHOD

This application is a National Stage Entry of PCT/JP2016/001421 filed on Mar. 14, 2016, which claims priority from Japanese Patent Application 2015-057047 filed on Mar. 20, 2015, the contents of all of which are incorporated herein by reference, in their entirety.

TECHNICAL FIELD

The present invention relates to a technique to remotely determine the status of defects or the like caused in a structure.

BACKGROUND ART

Defects (cracks, separations, or internal cavities) caused on the surface of a concrete structure such as tunnels and bridges are known to affect the soundness of the structure. It is thus necessary to accurately detect these defects so as to accurately judge the soundness of a structure.

Detection of defects of a structure such as cracks, separations, or internal cavities has been performed by an inspector's visual check or hammering tests, in which the inspector has to approach the structure for inspection. Therefore, increase in operation costs for preparing an environment to facilitate the aerial operation and economic opportunity loss due to traffic control required for setting the operational environment have presented a problem. In view of this, a method to enable an inspector to inspect a structure remotely is desired.

There is a method performed by image measurement has been proposed as a method to determine a structure status remotely. For example, a technique has been proposed to subject an image of a structure captured by an image-capturing device, to binarization processing with a predetermined threshold value, and detect a portion of the binarized image corresponding to a crack (PTL 1). There has been also proposed a technique to detect a cleavage caused in a structure, from the stress state of the structure (PTL 2, PTL 3). There have also been proposed a system that determines a failure of an object to be measured by automatically analyzing the captured image by using both of an infrared image-capturing device or a visible-light image-capturing device, and a laser image-capturing device (PTL 4), and a method to create a defect map from the image captured by image-capturing means that is excellent in portability (PTL 5). Furthermore, in NPL 1, a method to enhance the accuracy in detecting a crack by detecting the motion of the cracked area, in the moving image of the surface of a structure.

CITATION LIST

Patent Literature

[PTL 1] Japanese Patent Application Publication No. 2003-035528
[PTL 2] Japanese Patent Application Publication No. 2008-232998
[PTL 3] Japanese Patent Application Publication No. 2006-343160
[PTL 4] Japanese Patent Application Publication No. 2004-347585
[PTL 5] Japanese Patent Application Publication No. 2002-236100
[PTL 6] Japanese Patent Application Publication No. 2012-132786

Non Patent Literature

[NPL 1] Z. Wang, et al., "Crack-opening displacement estimation method based on sequence of motion vector field images for civil infrastructure deterioration inspection", Image Media Processing Symposium (PCSJ/IMPS2014), 1-1-17, The Institute of Electronics, Information and Communication Engineers, Nov. 12, 2014

SUMMARY OF INVENTION

Technical Problem

However, with the above-mentioned techniques, for example when capturing an image of the lower surface of a structure such as a bridge, a displacement (referred to as "out-of-plane displacement") caused by movement of the location of the surface to be image-captured in the normal direction of the surface, due to deflection of the structure by means of loading will be added to a displacement (referred to as "in-plane displacement") of the surface in the in-plane direction having information of the defect of the structure. Accordingly, there is a problem of accuracy degradation in detection of a defect in a structure.

PTL 6 proposes, in measuring the strain caused on a surface of an object to be measured, a method to correct the out-of-plane displacement amount based on the displacement of a captured image. In PTL 6, the out-of-plane displacement amount is read from the side images before and after the deformation of the structure. For performing this, two video devices are provided, namely, a first video device that captures an image of the surface of the structure and a second video device that captures the side of the structure.

However, with this method, an extra video device to capture an image of the side becomes necessary other than a video device that captures an image of the surface, which increases costs. Furthermore, in case of bridges or the like, it becomes necessary to fix the image-capturing device and to assure the footing of the operators, so as to measure the side of the bridges or the like, which involves unfavorable operability and reduces the accuracy in measurement.

The present invention has been made in view of the above problems, and has an objective to detect with favorable accuracy any defect of a structure, such as cracks, separations, or internal cavities, remotely without contact, while restraining costs.

Solution to Problem

A status determination device according to the present invention comprises: a displacement calculation unit that, from time-series images of a structure surface before and after loading application, calculates a two-dimensional spatial distribution of a displacement of the time-series images; a correction amount calculation unit that calculates a correction amount based on a moving amount of the structure surface in a normal direction due to the loading application, from the two-dimensional spatial distribution of the displacement of the time-series images; a displacement correction unit that extracts a two-dimensional spatial distribution of a displacement of the structure surface, by subtracting the correction amount from the two-dimensional spatial distribution of the displacement of the time-series images; and an abnormality determination unit that identifies a defect of the structure, based on comparison between the two-dimensional spatial distribution of the displacement of the structure surface and a prepared spatial distribution of a displacement having been prepared in advance.

A status determination system according to the present invention comprises: a status determination device that includes: a displacement calculation unit that, from time-series images of a structure surface before and after loading application, calculates a two-dimensional spatial distribution of a displacement of the time-series images; a correction amount calculation unit that calculates a correction amount based on a moving amount of the structure surface in a normal direction due to the loading application, from the two-dimensional spatial distribution of the displacement of the time-series images; a displacement correction unit that extracts a two-dimensional spatial distribution of a displacement of the structure surface, by subtracting the correction amount from the two-dimensional spatial distribution of the displacement of the time-series images; and an abnormality determination unit that identifies a defect of the structure, based on comparison between the two-dimensional spatial distribution of the displacement of the structure surface and a prepared spatial distribution of a displacement having been prepared in advance; and an image-capturing unit that captures the time-series images and provides the status determination device with the time-series images.

A status determination method according to the present invention comprises: calculating, from time-series images of a structure surface before and after loading application, a two-dimensional spatial distribution of a displacement of the time-series images; calculating a correction amount based on a moving amount of the structure surface in a normal direction due to the loading application, from the two-dimensional spatial distribution of the displacement of the time-series images; extracting a two-dimensional spatial distribution of a displacement of the structure surface, by subtracting the correction amount from the two-dimensional spatial distribution of the displacement of the time-series images; and identifying a defect of the structure, based on comparison between the two-dimensional spatial distribution of the displacement of the structure surface and a prepared spatial distribution of a displacement having been prepared in advance.

Advantageous Effects of Invention

The present invention enables detection with favorable accuracy any defect of a structure, such as cracks, separations, or internal cavities, remotely without contact, while restraining costs.

BRIEF DESCRIPTION OF DRAWINGS

FIG. 6 is a diagram for explaining the relationship between an out-of-plane displacement vector, an in-plane displacement vector, and a measurement vector.

FIG. 12A is a diagram illustrating a distribution of the stress field around a crack.

FIG. 12B is a diagram illustrating a distribution of the stress field around a crack.

FIG. 14A is a diagram for explaining a pattern matching with a displacement distribution (a pattern in X-direction of the displacement) by an abnormality determination unit.

FIG. 14B is a diagram for explaining a pattern matching with a displacement distribution (a pattern in Y-direction of the displacement) by the abnormality determination unit.

FIG. 14C is a diagram for explaining a pattern matching with a displacement distribution (a pattern of a differential vector field of a displacement) by the abnormality determination unit.

FIG. 15B is a plan view illustrating a two-dimensional distribution of a stress on a surface viewed along the image-capturing direction when there is an internal cavity.

DESCRIPTION OF EMBODIMENTS

The following describes example embodiments of the present invention with reference to the drawings. Although the example embodiments described below provide technologically desirable limitations for practicing the present invention, the scope of the invention is not limited to the following limitations.

Figure 1:
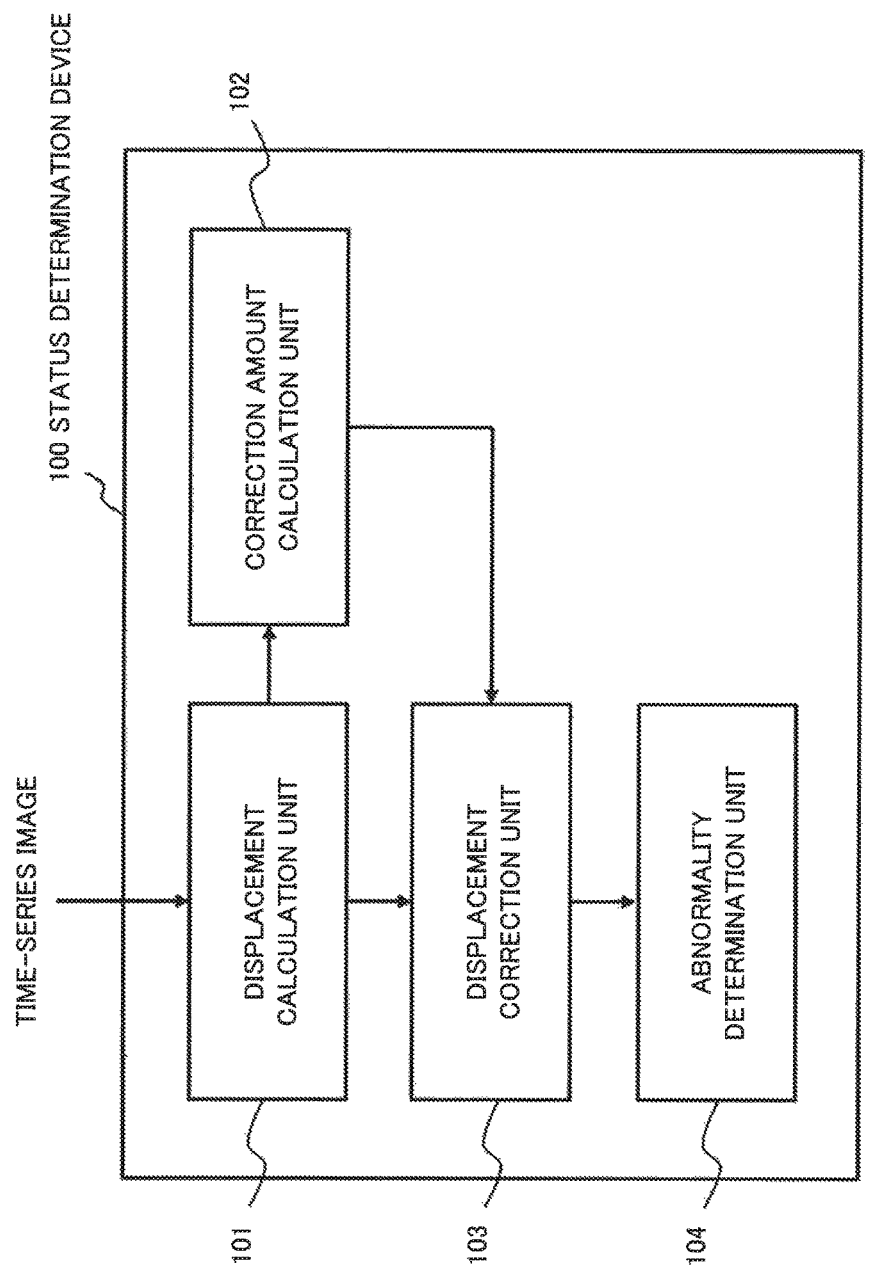
FIG. 1 is a block diagram illustrating a configuration of a status determination device according to an example embodiment of the present invention.

FIG. 1 is a block diagram illustrating a configuration of a status determination device according to an example embodiment of the present invention. The status determination device 100 according to the present example embodiment includes a displacement calculation unit 101 that calculates a two-dimensional spatial distribution of a displacement in time-series images taken before and after loading is applied on a surface of a structure, from the time-series images. In addition, the status determination device 100 according to the present example embodiment includes a correction amount calculation unit 102 that calculates a correction amount based on a moving amount of the structure surface in the normal direction due to loading application, from the two-dimensional spatial distribution of the displacement of the time-series images. In addition, the status determination device 100 according to the present example embodiment includes a displacement correction unit 103 that extracts a two-dimensional spatial distribution of the displacement of the structure surface, by subtracting the correction amount from the two-dimensional spatial distribution of the displacement of the time-series images. In addition, the status determination device 100 according to the present example embodiment includes an abnormality determination unit 104 that identifies defects in the structure based on a comparison between the two-dimensional spatial distribution of a displacement of the structure surface and a spatial distribution of a displacement prepared in advance. Note that the direction of the arrows in FIG. 1 is an example, and is not intended to limit the direction of the signals between the blocks.

Figure 2:
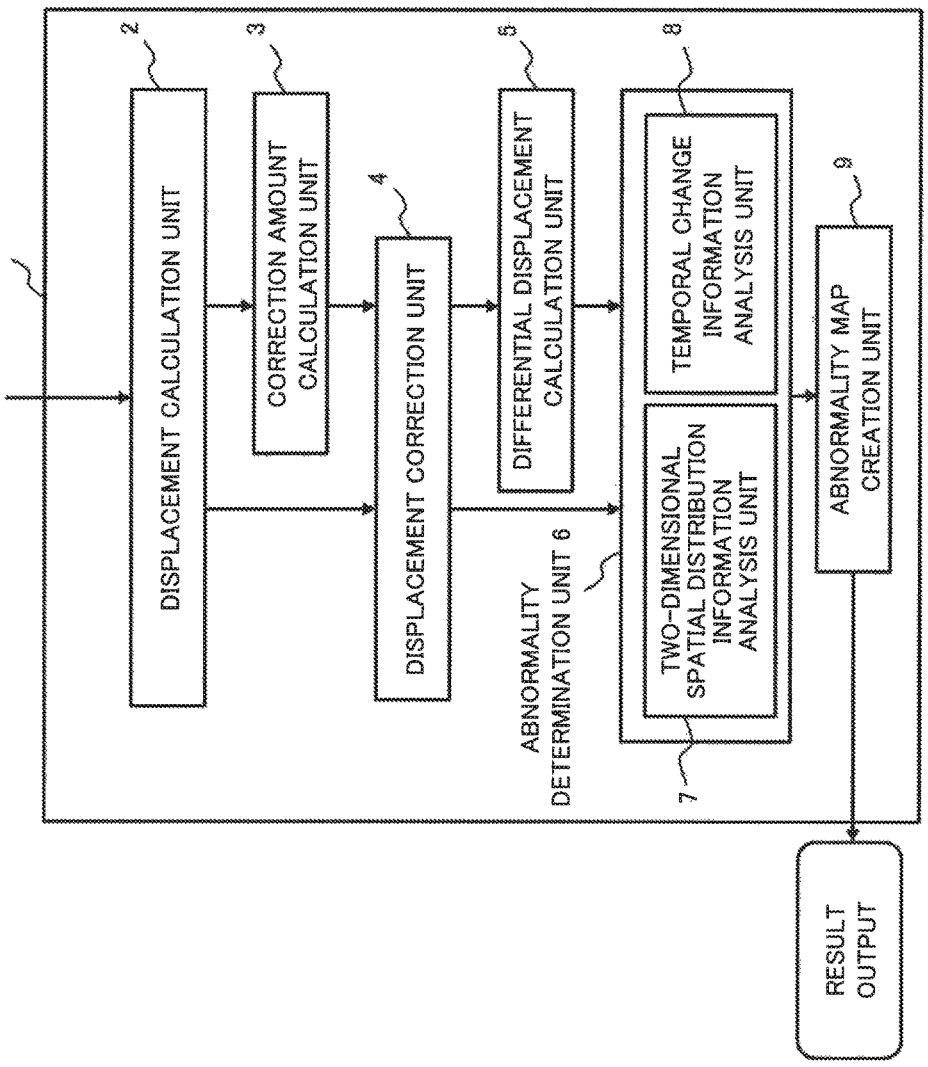
FIG. 2 is a block diagram illustrating a specific configuration of a status determination device according to an example embodiment of the present invention.

FIG. 2 is a block diagram illustrating a specific configuration of a status determination device according to an example embodiment of the present invention. The status determination device 1 includes a displacement calculation unit 2, a correction amount calculation unit 3, a displacement correction unit 4, a differential displacement calculation unit 5, an abnormality determination unit 6, and an abnormality map creation unit 9. The abnormality determination unit 6 includes a two-dimensional spatial distribution information analysis unit 7 and a temporal change information analysis unit 8. Note that the direction of the arrows in FIG. 2 is an example, and is not intended to limit the direction of the signals between the blocks.

Figure 3:
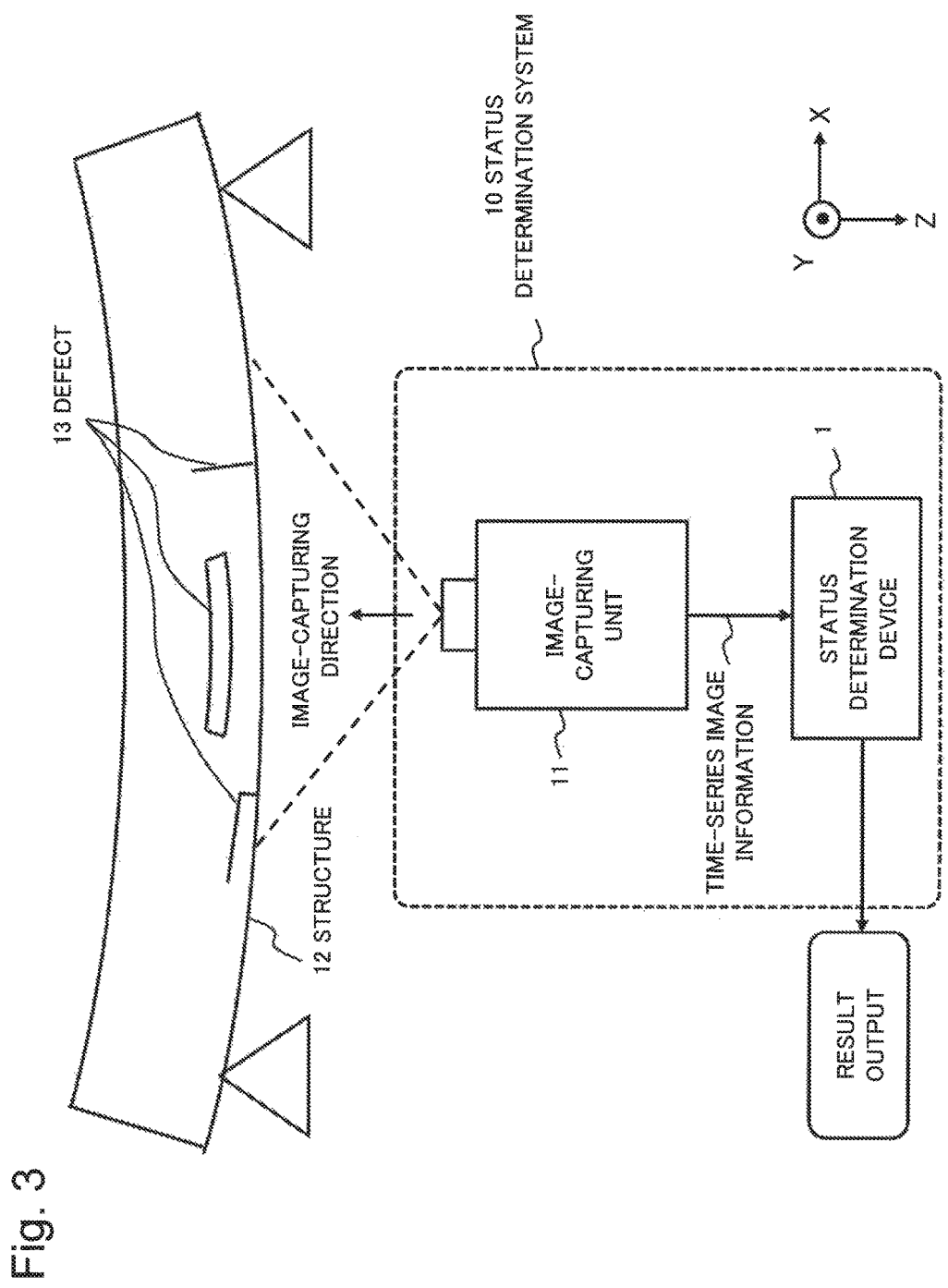
FIG. 3 is a block diagram illustrating a configuration of a status determination system according to an example embodiment of the present invention.

FIG. 3 is a block diagram illustrating a configuration of a status determination system according to an example embodiment of the present invention. The status determination system 10 includes a status determination device 1 and an image-capturing unit 11. The status determination device 1 is a device illustrated in FIG. 2. The image-capturing unit 11 is an image-capturing camera. The image-capturing unit 11 captures an image of a surface of a structure 12 before and after loading is applied on the structure 12, as the time-series images on the X-Y plane, and inputs the captured time-series images to the displacement calculation unit 2 of the status determination device 1. The status determination device 1 obtains time-series image information from the image-capturing unit 11. In FIG. 3, the structure 12, which is an object to be measured, is assumed to be a beam-like structure supported at two points. The structure 12 may have various types of defects 13. Note that the direction of the arrows in FIG. 3 is an example, and is not intended to limit the direction of the signals between the blocks.

The displacement calculation unit 2 of the status determination device 1 calculates a displacement for each (X, Y) coordinate on the X-Y plane of the time-series images. That is, by using, as a reference, the frame image before loading application which was captured by the image-capturing unit 11, the displacement of the frame image at the initial time after loading application is calculated. Then, the displacement of the frame image at the subsequent time after loading application is calculated, and the displacement of the frame image at the further subsequent time is calculated, and so on, to calculate the displacement from the image before loading application for each time-series image. The displacement calculation unit 2 can calculate a displacement using an image correlation operation. The displacement calculation unit 2 may also represent a displacement distribution diagram of the calculated displacement, as a two-dimensional spatial distribution on the X-Y plane.

From the two-dimensional spatial distribution of the displacement of the time-series images calculated by the displacement calculation unit 2, the correction amount calculation unit 3 calculates a displacement (referred to as "out-of-plane displacement") that is included in the displacement calculated by the displacement calculation unit 2 and that has been caused by moving of the surface of the structure 12 in its normal direction which is attributed to the deflection of the structure 12 and the like.

The displacement correction unit 4 extracts a displacement (referred to as "in-plane displacement") caused on a surface of the structure 12, by subtracting the out-of-plane displacement calculated by the correction amount calculation unit 3, either from the displacement calculated by the displacement calculation unit 2 or the displacement distribution diagram. The displacement correction unit 4 inputs the extracted in-plane displacement to the differential displacement calculation unit 5 and to the abnormality determination unit 6.

The differential displacement calculation unit 5 performs spatial differential on either the displacement or the displacement distribution diagram, to calculate either a differential displacement or a differential displacement distribution diagram in which the calculated differential displacement is plotted as the two-dimensional differential spatial distribution on the X-Y plane. The calculation results of the displacement correction unit 4 and the differential displacement calculation unit 5 are input to the abnormality determination unit 6.

The abnormality determination unit 6 determines the status of the structure 12 based on the input calculation results. That is, the abnormality determination unit 6 determines the location and type of the abnormality (defect 13) of the structure 12, from the analysis results of the two-dimensional spatial distribution information analysis unit 7 and the temporal change information analysis unit 8. Further, the abnormality determination unit 6 inputs the determined location and type of the abnormality of the structure 12, to the abnormality map creation unit 9. The abnormality map creation unit 9 maps the spatial distribution of the abnormal status of the structure 12 on the X-Y plane, records it as an abnormality map, and outputs the abnormality map.

The status determination device 1 can be an information appliance such as a personal computer (PC) and a server. Each unit that constitutes a status determination device 1 can be realized by operating a CPU (central processing unit), being an operational resource, and a memory and an HDD (hard disk drive), being a storage resource, included in the information appliance, to operate a program in the CPU.

Figure 4A:
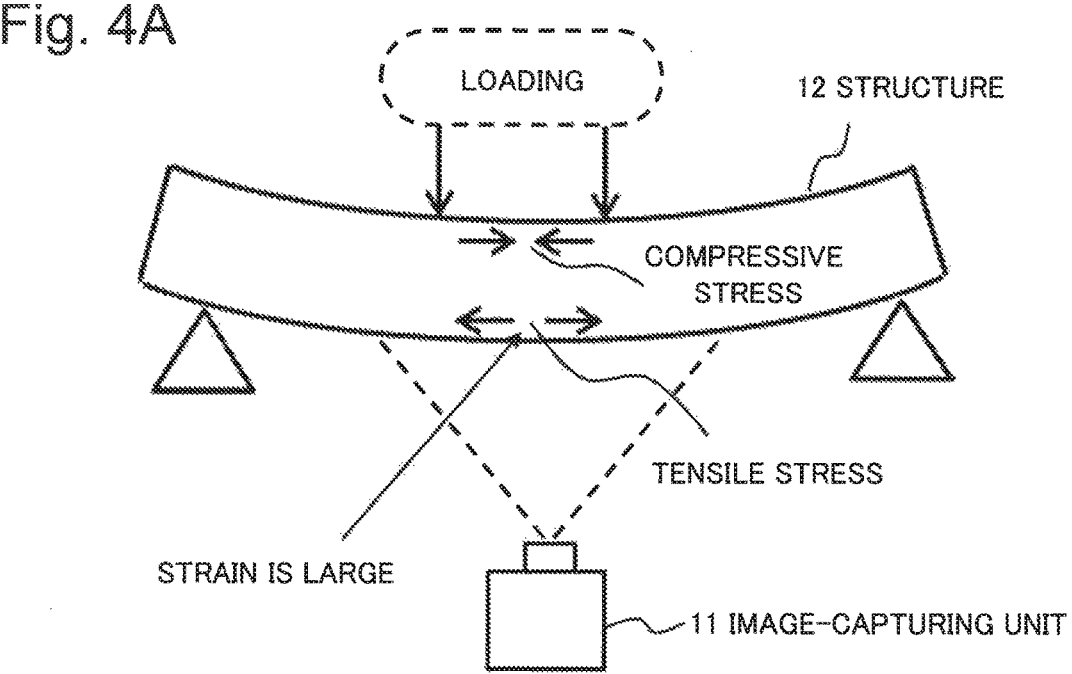
FIG. 4A is a diagram for explaining a relation between the structure status (sound case) and the displacement of the surface.

FIG. 4A to FIG. 4D are diagrams for explaining a relation between various abnormality statuses of the structure 12 and the in-plane displacement of the surfaces. FIG. 4A is a side view of the structure 12 having a beam-like form supported at two points. As illustrated in FIG. 4A, the image-capturing unit 11 as illustrated in FIG. 3 is placed under a condition to capture an image of a lower surface of the structure 12 in the image-capturing direction (Z-direction). Under this condition, if the structure 12 is in a sound condition, upon application of perpendicular loading from above the upper surface of the structure 12, a compressive stress is applied onto the upper surface of the structure 12, and a tensile stress is applied onto the lower surface thereof, as illustrated in FIG. 4A. Note that the structure 12 is not necessarily a beam-like structure which is supported at two points, as long as similar stresses are exerted on the structure.

Here, when the structure 12 is an elastic body, a stress is proportional to a strain. Its Young's modulus, being the factor of proportionality, depends on the material of the structure. Because a strain that is proportional to a stress is a displacement per unit length, the differential displacement calculation unit 5 can calculate the strain by performing spatial differential on the result obtained by calculation by the displacement correction unit 4. That is, a stress field can be obtained by the result of the differential displacement calculation unit 5.

Figure 4B:
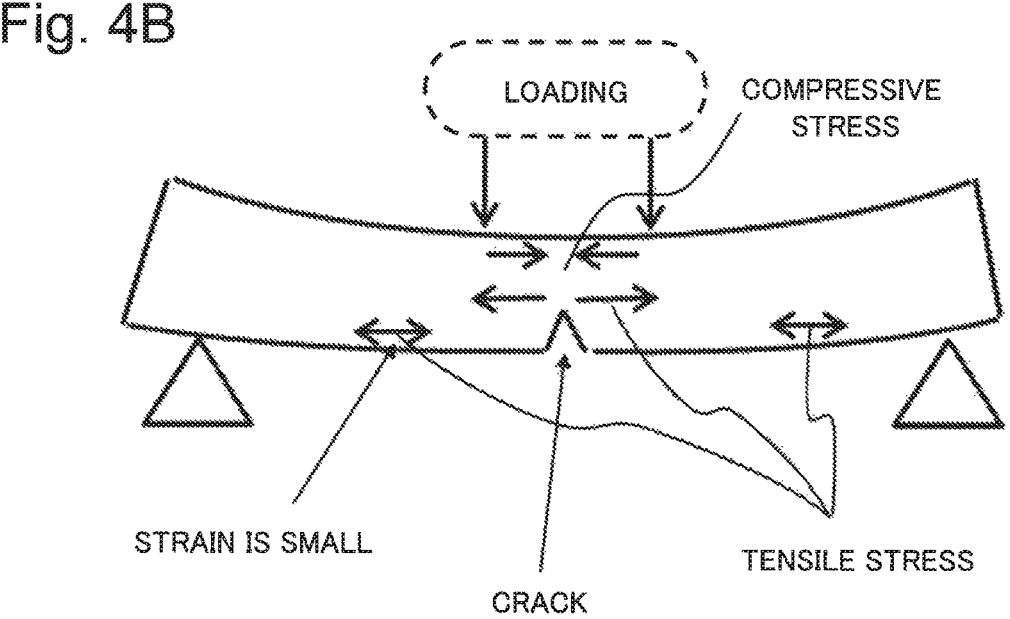
FIG. 4B is a diagram for explaining a relation between the structure status (crack case) and the displacement of the surface.

As illustrated in FIG. 4B, when there is a crack, the cracked portion is subject to a greater displacement due to loading. On the other hand, no stress is conveyed around the cracked portion, due to the cracked portion. Therefore, the tensile stress at the lower surface of the structure 12 is smaller than in a sound status illustrated in FIG. 4A.

Figure 4C:
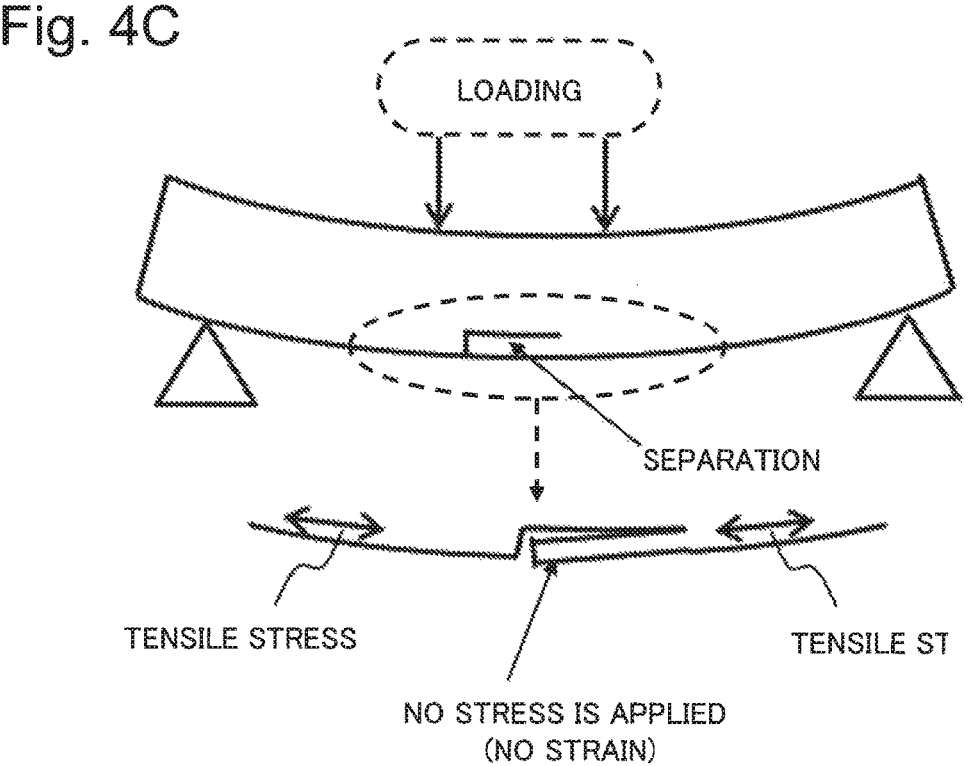
FIG. 4C is a diagram for explaining a relation between the structure status (separation case) and the displacement of the surface.

When there is a separation, the outer appearance of the structure 12 when viewed from the lower surface looks similar to as in the case of cracks, as illustrated in FIG. 4C. However, in case of a separation, no stress is conveyed from the separated portion to the portion above the separated portion. Therefore, the displacement due to loading at the separated portion only moves in parallel in a certain amount and in a certain direction, and no strain, being its spatial differential value, will be caused. Accordingly, a crack can be distinguished from a separation, by using information on the strain obtained by performing spatial differential on the displacement due to loading.

Figure 4D:
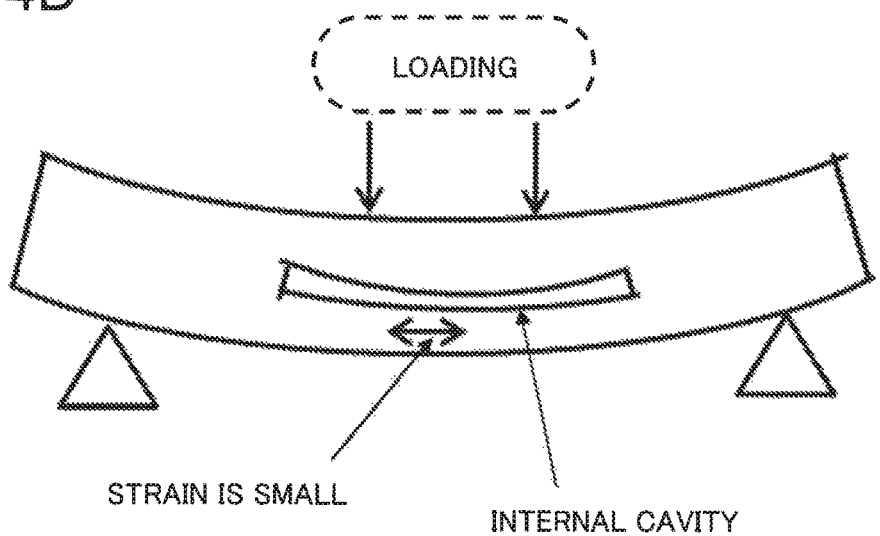
FIG. 4D is a diagram for explaining a relation between the structure status (internal cavity case) and the displacement of the surface.

When there is an internal cavity as illustrated in FIG. 4D, the conveyance of a stress is inhibited in the case of internal cavities, and the stress is reduced at the lower surface of the structure 12. The strain calculated from the image will accordingly be reduced. Therefore, it is possible to find an internal cavity that cannot be directly found from outside of the structure 12.

The displacement of the structure surface to be measured in FIG. 4A to FIG. 4D is an in-plane displacement (X-direction and Y-direction) within the X-Y plane. Therefore, the correction amount calculation unit 3 calculates the apparent displacement (out-of-plane displacement) caused when the surface of the structure 12 moves in its normal direction due to loading as a correction amount, and the displacement correction unit 4 subtracts the out-of-plane displacement therefrom, to extract an in-plane displacement. The following describes a method to calculate an out-of-plane displacement in the correction amount calculation unit 3.

Note that the term "normal line" is used for a curved surface. When one large curved surface is formed overall, and a plurality of small curves are formed on the large curved surface, the normal line is deemed to mean the normal line of the large curved surface. Normally, for a plane surface, the term "perpendicular line" is used. However, in the following description, the term "normal line" is used also in the case of a plane surface, for the sake of simplicity.

Figure 5:
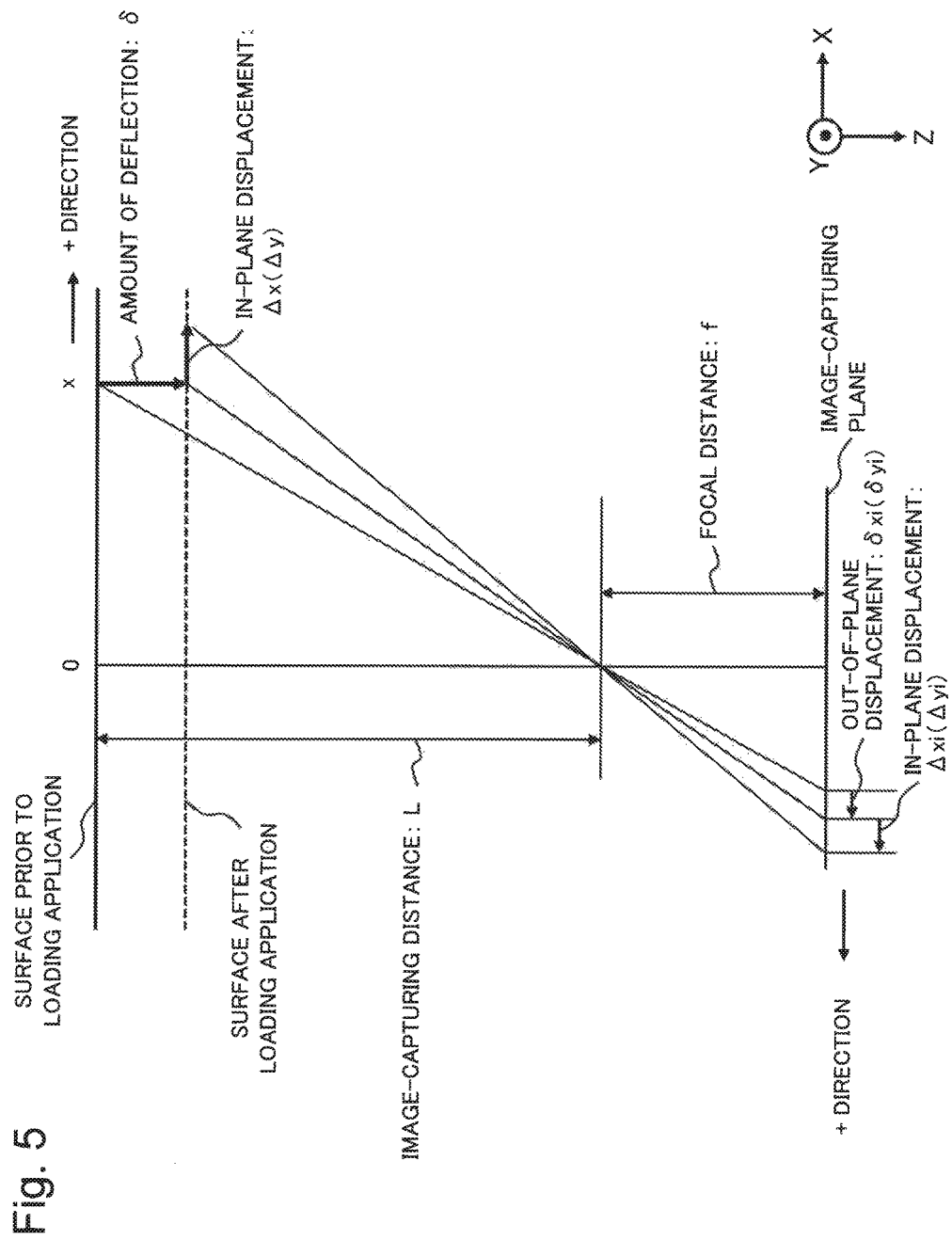
FIG. 5 is a diagram for explaining an out-of-plane displacement at the time of image-capturing a lower surface of the structure, when the structure is deflected attributed to loading.

FIG. 5 is a diagram for explaining an out-of-plane displacement at the time of image-capturing a lower surface of the structure, when the structure 12 is deflected attributed to loading (Please refer to FIG. 3). In FIG. 5, the moving amount of the surface of the structure 12 in its normal direction (Z-direction) is deemed to be caused by deflection of the structure, and is denoted as the amount of deflection $\delta$. Note that the moving amount of a surface in Z-direction is not limited to the amount of deflection, and can include an amount by which the entire structure 12 is moved by going downward attributed to loading, for example.

As illustrated in FIG. 5, when loading causes a deflection (the amount of deflection $\delta$) on the structure 12, in X-direction of the image-capturing unit 11 on the image-capturing plane, an out-of-plane displacement $\delta x_i$ is caused due to the amount of deflection $\delta$, separate from $\Delta x_i$ that corresponds to the in-plane displacement $\Delta x$ being the two-dimensional spatial distribution of the displacement of the structure surface. Likewise, in Y-direction, $\Delta y_i$ that corresponds to the in-plane displacement $\Delta y$ and the out-of-plane displacement $\delta y_i$ due to the amount of deflection $\delta$ are caused. Let "L" be the image-capturing distance, let "f" be the lens focal distance, and let (x, y) be the coordinates with its origin being the center of image-capturing on the structure surface. Then, the out-of-plane displacement $\delta x_i$, $\delta y_i$, and the in-plane displacement $\Delta x_i$, $\Delta y_i$ are respectively represented as in the following Expressions 1, 2, 3, and 4.

[Math. 1]
$$\delta x_i = f\left(\frac{1}{L-\delta} - \frac{1}{L}\right)x \quad \text{(Expression 1)}$$

[Math. 2]
$$\delta y_i = f\left(\frac{1}{L-\delta} - \frac{1}{L}\right)y \quad \text{(Expression 2)}$$

[Math. 3]
$$\Delta x_i = \frac{f}{L-\delta}\Delta x \quad \text{(Expression 3)}$$

[Math. 4]
$$\Delta y_i = \frac{f}{L-\delta}\Delta y \quad \text{(Expression 4)}$$

For example, when the amount of deflection $\delta$ after loading on the structure 12 compared to before loading is 4 mm, the image-capturing distance L is 5 m, and the lens focal distance f is 50 mm, and when the distance x from the image-capturing center on the surface of the structure 12 is 200 mm, the out-of-plane displacement $\delta x_i$ of the image-capturing plane is 1.6 μm, from Expression 1. When there is an in-plane displacement $\Delta x$ of 160 μm on the surface of the structure 12, the in-plane displacement $\Delta x_i$ of the image-capturing plane is 1.6 μm, from Expression 3. In this way, an out-of-plane displacement equal to an in-plane displacement is likely superposed on the displacement of the time-series images calculated by the displacement calculation unit 2 and the displacement distribution diagram depicting the two-dimensional spatial distribution on the X-Y plane.

Here, by summarizing Expression 1 and Expression 2 as an out-of-plane displacement vector $\delta i(\delta x_i, \delta y_i)$; and summarizing Expression 3 and Expression 4 as an in-plane displacement vector $\Delta i(\Delta x_i, \Delta y_i)$, the following Expression 5 and Expression 6 result.

[Math. 5]
$$\delta i(\delta x_i, \delta y_i) = \left(f\left(\frac{1}{L-\delta}-\frac{1}{L}\right)x, f\left(\frac{1}{L-\delta}-\frac{1}{L}\right)y\right) \quad \text{(Expression 5)}$$

[Math. 6]
$$\Delta i(\Delta x_i, \Delta y_i) = \left(\frac{f}{L-\delta}\Delta x, \frac{f}{L-\delta}\Delta y\right) \quad \text{(Expression 6)}$$

FIG. 6 is a diagram illustrating the relationship between an out-of-plane displacement vector $\delta i(\delta x_i, \delta y_i)$ and an in-plane displacement vector $\Delta i(\Delta x_i, \Delta y_i)$, which are represented by Expression 5 and Expression 6. In FIG. 6, the out-of-plane displacement vector $\delta i(\delta x_i, \delta y_i)$ is a radial vector group (the thin solid arrow in FIG. 6), and its magnitude R (x, y) is expressed as Expression 7, from Expression 1 and Expression 2. In Expression 7, if the amount of deflection $\delta$ is constant, its magnitude takes a value proportional to the distance from the image-capturing center. Let "k" be the factor of proportionality as denoted in Expression 8, Expression 7 can be expressed as Expression 9.

[Math. 7]
$$R(x, y) = \sqrt{\delta x_i(x, y)^2 + \delta y_i(x, y)^2} = f\left(\frac{1}{L-\delta}-\frac{1}{L}\right)\sqrt{x^2+y^2} \quad \text{(Expression 7)}$$

[Math. 8]
$$k = f\left(\frac{1}{L-\delta}-\frac{1}{L}\right) \quad \text{(Expression 8)}$$

[Math. 9]
$$R(x, y) = k\sqrt{x^2+y^2} \quad \text{(Expression 9)}$$

Here, the displacement distribution calculated by the displacement calculation unit 2 corresponds to a measurement vector V(Vx, Vy) (the dotted arrow in FIG. 6), which is a resultant vector between the out-of-plane displacement vector $\delta i(\delta x_i, \delta y_i)$ (the thin solid arrow in FIG. 6) and the in-plane displacement vector $\Delta i(\Delta x_i, \Delta y_i)$ (the bold solid arrow in FIG. 6). Let Rmes(x, y) be the magnitude of the measurement vector V(Vx, Vy). Then, Expression 10 and Expression 11 result.

[Math. 10]
$$Rmes(x,y) = \sqrt{Vx(x,y)^2 + Vy(x,y)^2} \quad \text{(Expression 10)}$$

[Math. 11]
$$V(V_x, V_y) = \Delta i(\Delta x_i, \Delta y_i) + (\delta x_i, \delta y_i) \quad \text{(Expression 11)}$$

Figure 7A:
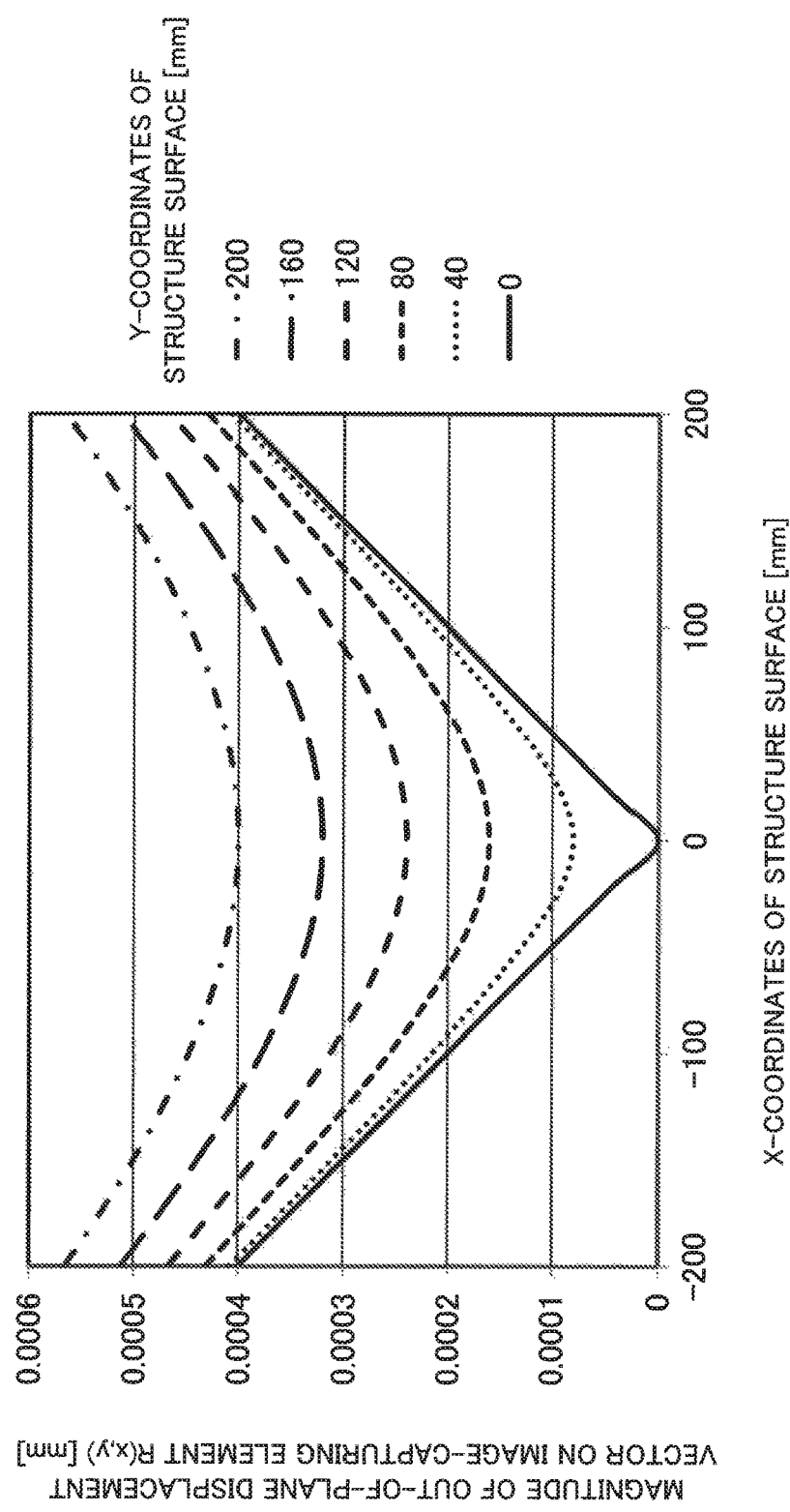
FIG. 7A is a diagram illustrating a graph of a magnitude of the out-of-plane displacement vector.
Figure 7B:
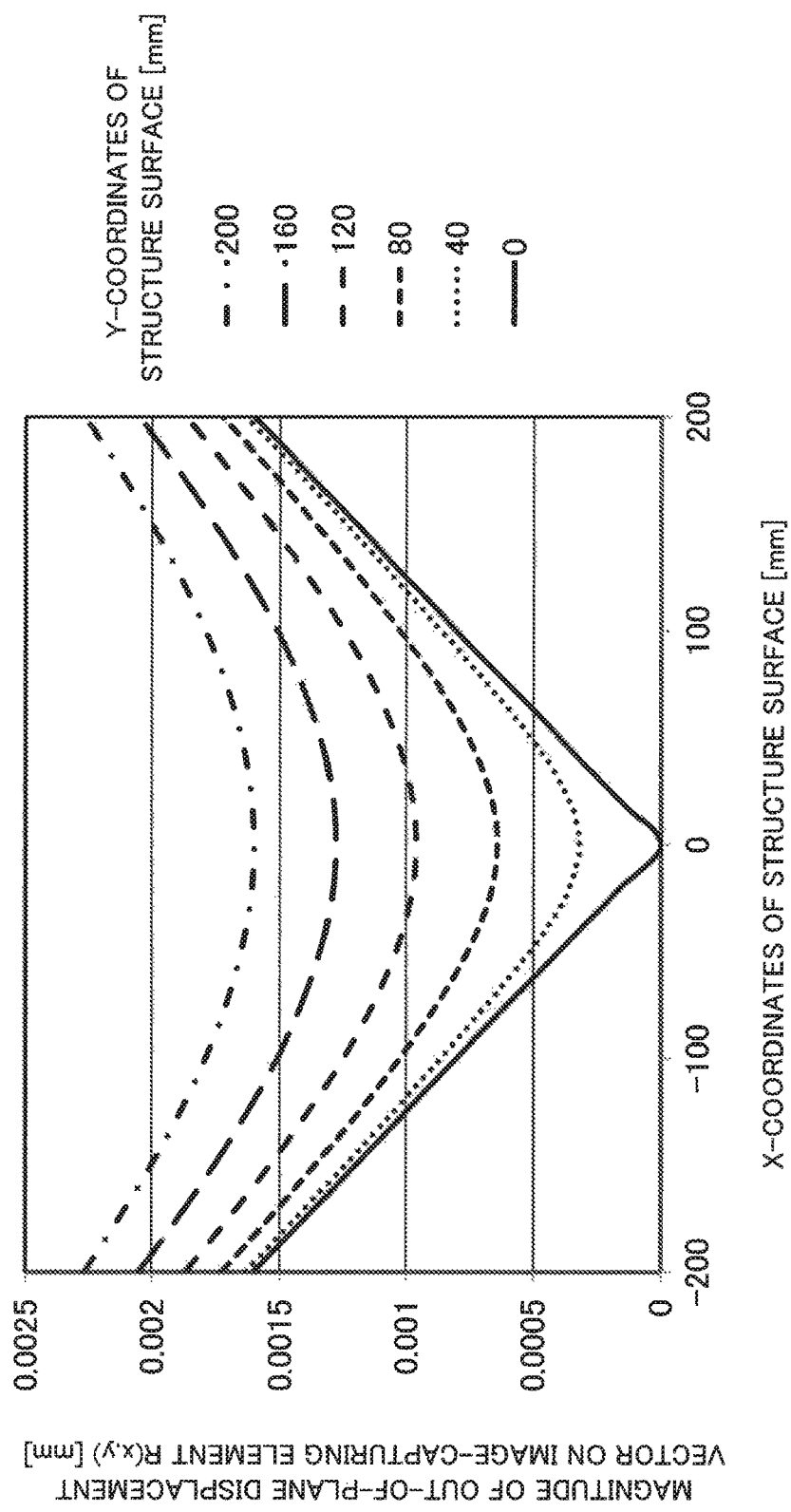
FIG. 7B is a diagram illustrating a graph of a magnitude of the out-of-plane displacement vector.

FIG. 7A and FIG. 7B are graphs depicting an example of the value of the magnitude R(x, y) of the out-of-plane displacement vector $\delta i(\delta x_i, \delta y_i)$ given by Expression 7, Expression 8, and Expression 9. FIG. 7A and FIG. 7B are graphs depicting the magnitude R(x, y) of the out-of-plane displacement vector when the amount of deflection $\delta$ is 1 mm and 4 mm, respectively. In each graph, the image-capturing distance L before deflection is 5000 mm, and the focal distance f is 50 mm. As can be understood by comparing the graphs of FIG. 7A and FIG. 7B, both graphs are similar figures to each other, and as the amount of deflection $\delta$ is larger, its enlargement factor increases. This enlargement factor corresponds to the factor of proportionality K given by Expression 8.

Figure 8:
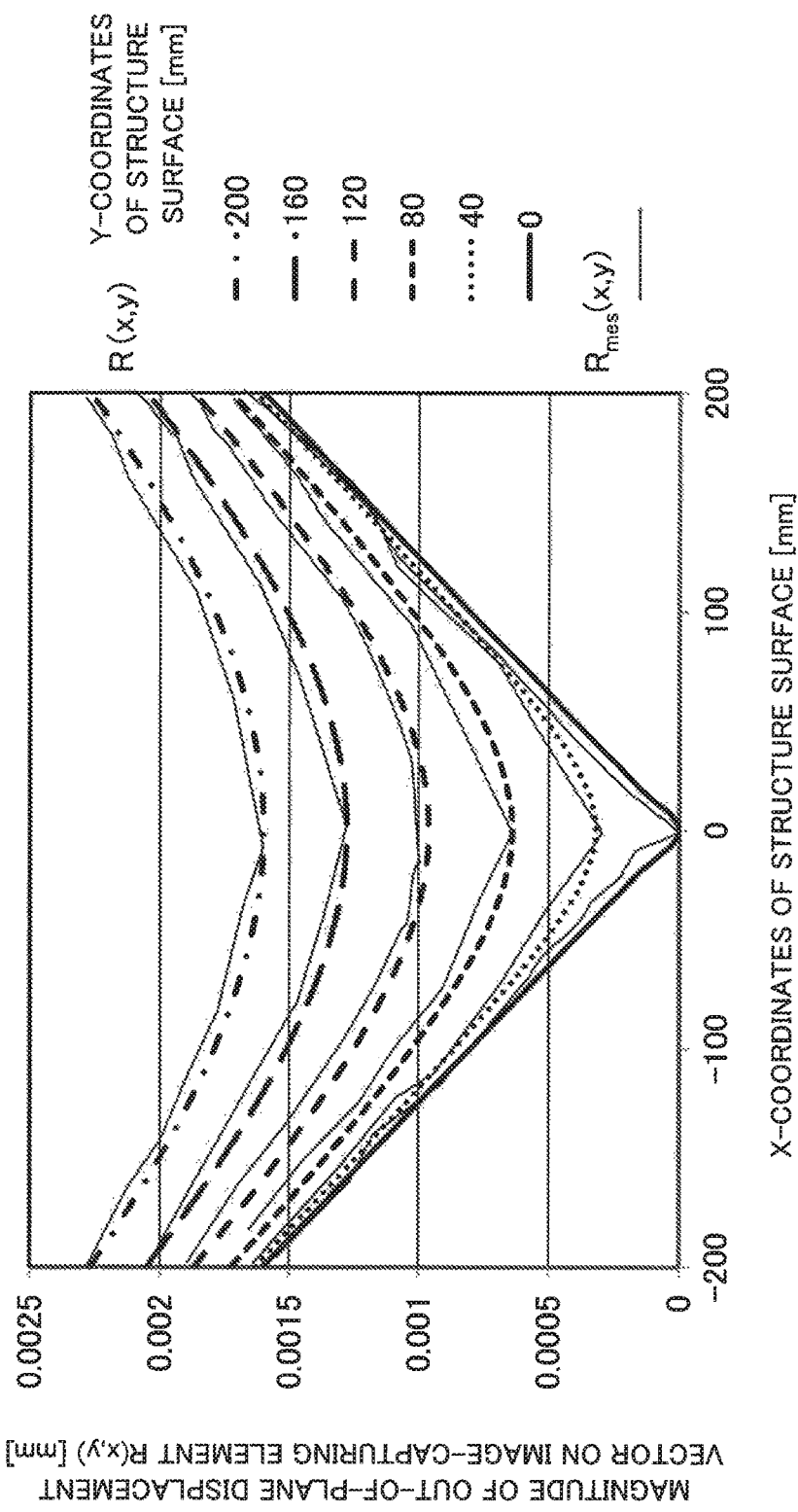
FIG. 8 is a diagram illustrating a magnitude of the out-of-plane displacement vector and a graph of a magnitude of the out-of-plane displacement vector.

FIG. 8 is a graph in which the magnitude Rmes(x, y) of the measurement vector V(Vx, Vy) is superposed on the graph in FIG. 7B. In FIG. 8, Rmes(x, y) is expressed by a thin solid line. Rmes(x, y) takes a form similar to the magnitude R(x, y) of the out-of-plane displacement vector, if the magnitude R(x, y) of the out-of-plane displacement vector is larger than the in-plane displacement vector $\Delta i(\Delta x_i, \Delta y_i)$, and therefore the enlargement factor of R(x, y) can be estimated from Rmes(x, y). The enlargement factor of R(x, y) is estimated by obtaining the factor of proportionality k at which the evaluation function E(k) depicted in Expression 12 is minimized.

[Math. 12]

$$E(k) = \sum_{x,y} \{R_{mes}(x, y) - R(x, y)\}^2 \qquad \text{(Expression 12)}$$

The intensity factor k in Expression 12 is calculated by the least-square method. The evaluation function E(k) may be sum of absolute values, other power sums, and the like, other than the sum of squares of the difference between Rmes(x, y) and R(x, y).

The correction amount calculation unit 3 estimates the out-of-plane displacement vector by performing an operation to convert the estimated enlargement factor k into an amount of deflection δ using Expression 8, to estimate the out-of-plane displacement vector. The displacement correction unit 4 extracts an in-plane displacement vector, by subtracting the out-of-plane displacement vector calculated by the correction amount calculation unit 3 as a correction amount, from the measurement vector obtained by the displacement calculation unit 2.

The following explains an example in which the in-plane displacement is extracted by calculating the out-of-plane displacement, and subtracting the calculated out-of-plane displacement from the measured displacement, taking an example in which the structure 12 has a crack along Y-direction as illustrated in FIG. 4B. In calculating a displacement by means of the displacement calculation unit 2, the time-series images obtained by image-capturing the lower surface of the structure 12 illustrated in FIG. 3 in the image-capturing direction illustrated in this drawing before and after loading application are used.

Here, the image-capturing distance is set to be 5 m, and the structure 12 is assumed to be a double-supported beam under the condition equivalent to when 10 tons of loading is applied, which is made of concrete (Young's modulus of 40 GPa) and has a length of 20 m, a thickness of 0.5 m, and a width of 10 m. The area of the image at which the displacement is measured is assumed to be in the range of ±200 mm both in X-direction and Y-direction, with the cracked portion of the surface of the structure 12 serving as the image center.

An example assumes the lens focal distance of the camera of the image-capturing unit 11 to be 50 mm and the pixel pitch to be 5 µm, so as to obtain pixel resolution of 250 µm at the image-capturing distance of 5 m. The image-capturing element of the image-capturing unit 11 is monochroic and has 2000 pixels horizontally and 2000 pixels vertically, to enable image-capturing the range of 0.5 m×0.5 m at the image-capturing distance of 5 m. The frame rate of the image-capturing element is assumed to be 60 Hz. In addition, in the displacement calculation unit 2, the image correlation is conducted by sub-pixel displacement estimation by quadratic curve interpolation, to enable displacement estimation up to 1/100 pixels, and 2.5 µm displacement resolution.

When the above-described image-capturing unit 11 is used, the image displacement measurement area (in the range of −200 mm to 200 mm in both X-direction and Y-direction) will have 1600 pixels horizontally and 1600 pixels vertically. For this pixel area, the operations of Expression 1 to Expression 12 are conducted.

Figure 9A:
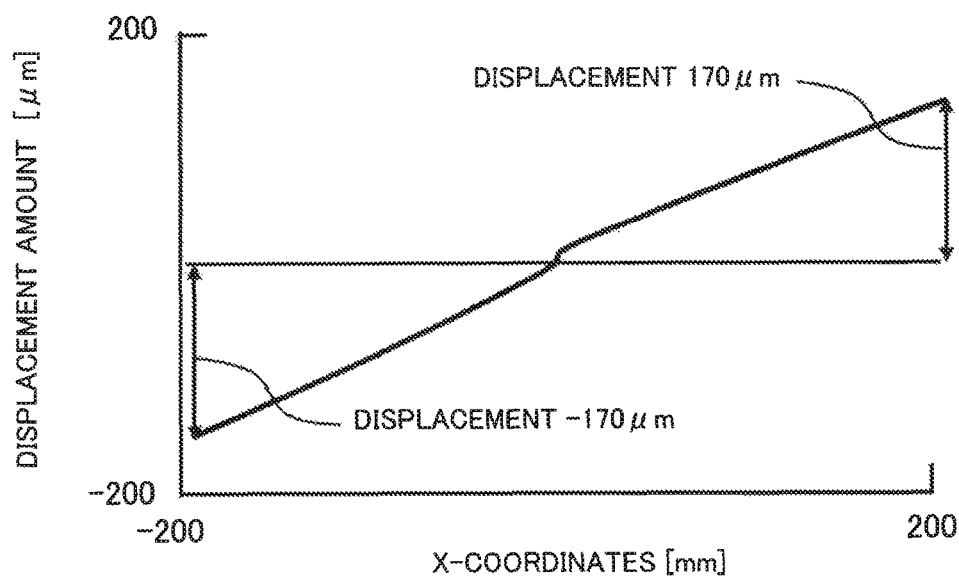
FIG. 9A is a diagram illustrating a result of calculating, in a displacement calculation unit, a displacement of a structure surface in X-direction after loading compared to before loading (crack case).
Figure 9B:
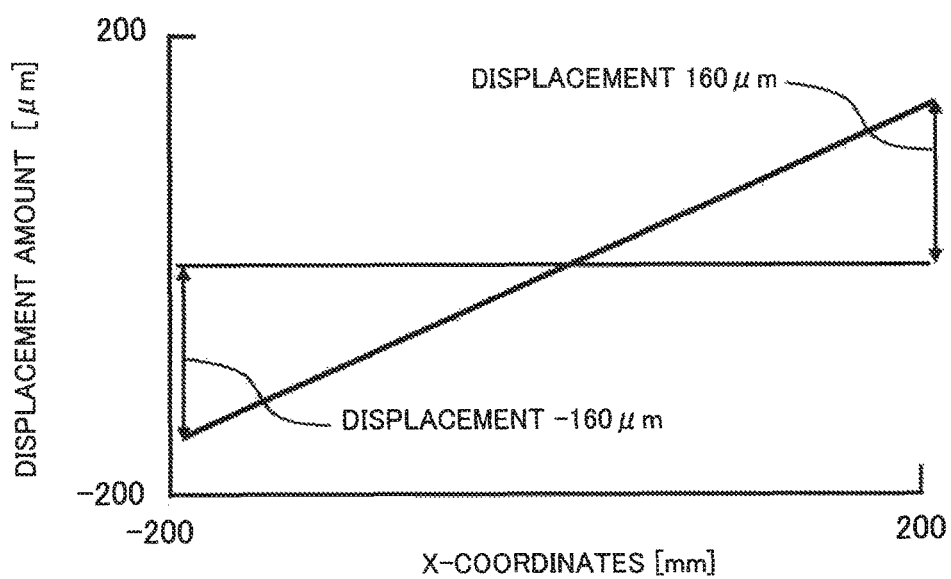
FIG. 9B is a diagram illustrating a result of calculating, in the displacement calculation unit, a displacement of the structure surface in Y-direction after loading compared to before loading (crack case).

FIG. 9A and FIG. 9B illustrate a displacement distribution in X-direction of the measurement vector V(Vx, Vy) when Y=0 mm and a displacement distribution in Y-direction when X=0 mm, which have been obtained by the displacement calculation unit 2, respectively. FIG. 9A and FIG. 9B are graphs in which the displacement obtained from Expression 6 is the displacement in the coordinates on the surface of the structure 12 to be measured, which do not take into consideration the out-of-plane displacement contained in the measurement vector V(Vx, Vy).

In FIG. 9A illustrating a displacement in X-direction, the displacement of ±170 µm is caused in the range of ±200 mm from the image capturing range. In FIG. 9B illustrating a displacement in Y-direction, the displacement of ±160 µm is caused as a straight line, in the range of ±200 mm from the image capturing range. The displacement in X-direction is a displacement on which the out-of-plane displacement is superposed on the in-plane displacement. On the other hand, the displacement in Y-direction is a displacement with only the out-of-plane displacement.

The factor of proportionality k at which the evaluation function E(k) in Expression 12 is minimized is obtained as 0.000008 using the measurement vector V(Vx, Vy) obtained in the displacement calculation unit 2 in the least-square method. When substituting this value in Expression 8, the amount of deflection δ is obtained to be 4 mm. By substituting this amount of deflection δ in Expression 5, the out-of-plane displacement vector δi(δx$_i$, δy$_i$) is obtained. This result is input to the displacement correction unit 4 as an output of the correction amount calculation unit 3.

The displacement correction unit 4 obtains the in-plane displacement vector Δi(Δx$_i$, Δy$_i$) by subtracting the out-of-plane displacement vector δi(δx$_i$, δy$_i$) obtained in the correction amount calculation unit 3 from the measurement vector V(Vx, Vy) obtained in the displacement calculation unit 2, and calculates the in-plane displacements for X-direction and Y-direction from Expression 6.

Figure 10A:
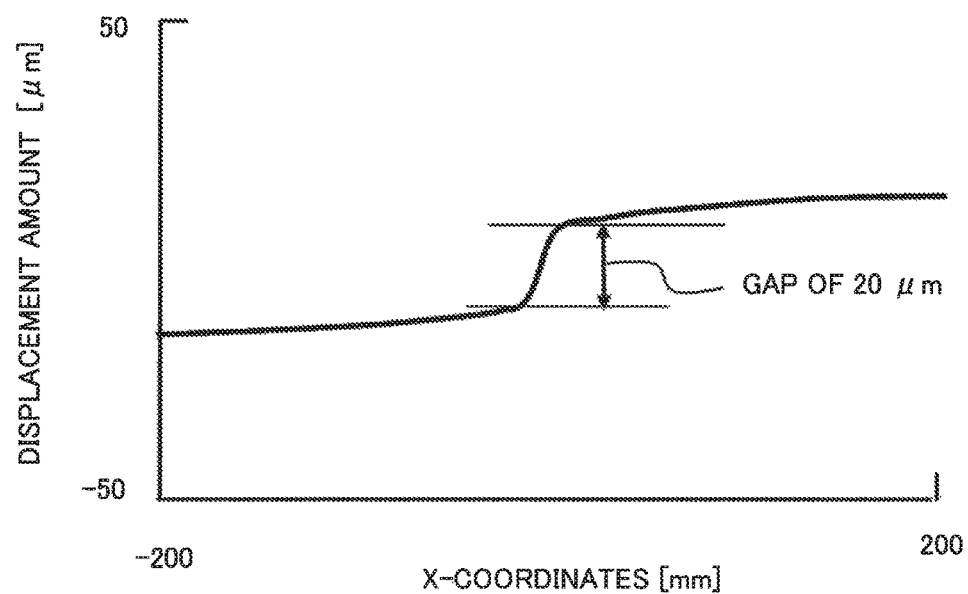
FIG. 10A is a diagram illustrating a result of calculating, in a displacement correction unit, an in-plane displacement of the structure surface in X-direction after loading compared to before loading (crack case).
Figure 10B:
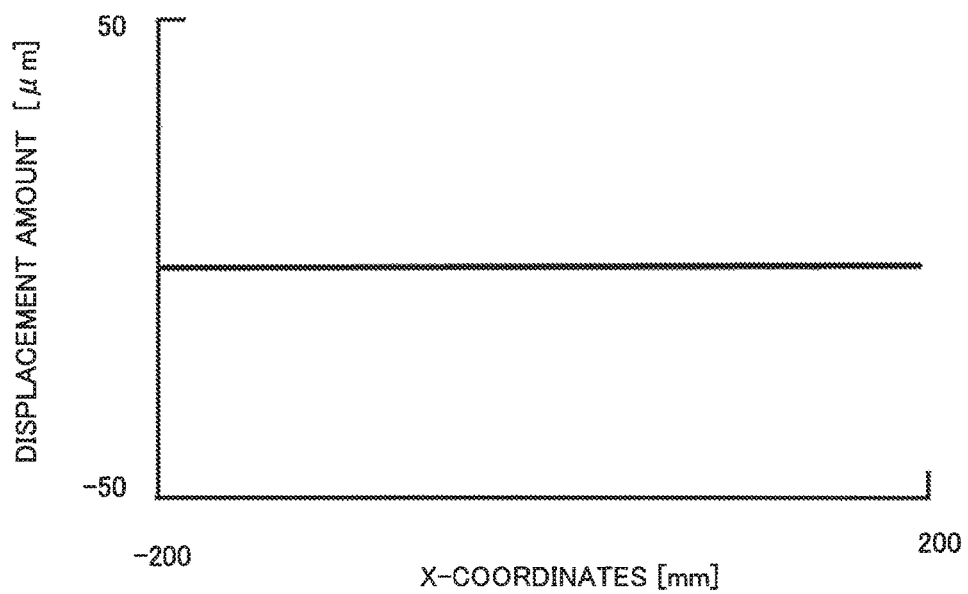
FIG. 10B is a diagram illustrating a result of calculating, in the displacement correction unit, an in-plane displacement of the structure surface in Y-direction after loading compared to before loading (crack case).

FIG. 10A and FIG. 10B illustrate an output of the displacement correction unit 4. FIG. 10A is a graph depicting a displacement in X-direction, which illustrates occurrence of a steep and discontinuous displacement of 20 µm in the cracked portion. On the other hand, FIG. 10B is a graph depicting a displacement in Y-direction, in which the displacement is 0. As in FIG. 10A and FIG. 10B, the in-plane displacement on the structure surface can be extracted by being separated from the out-of-plane displacement.

Figure 11:
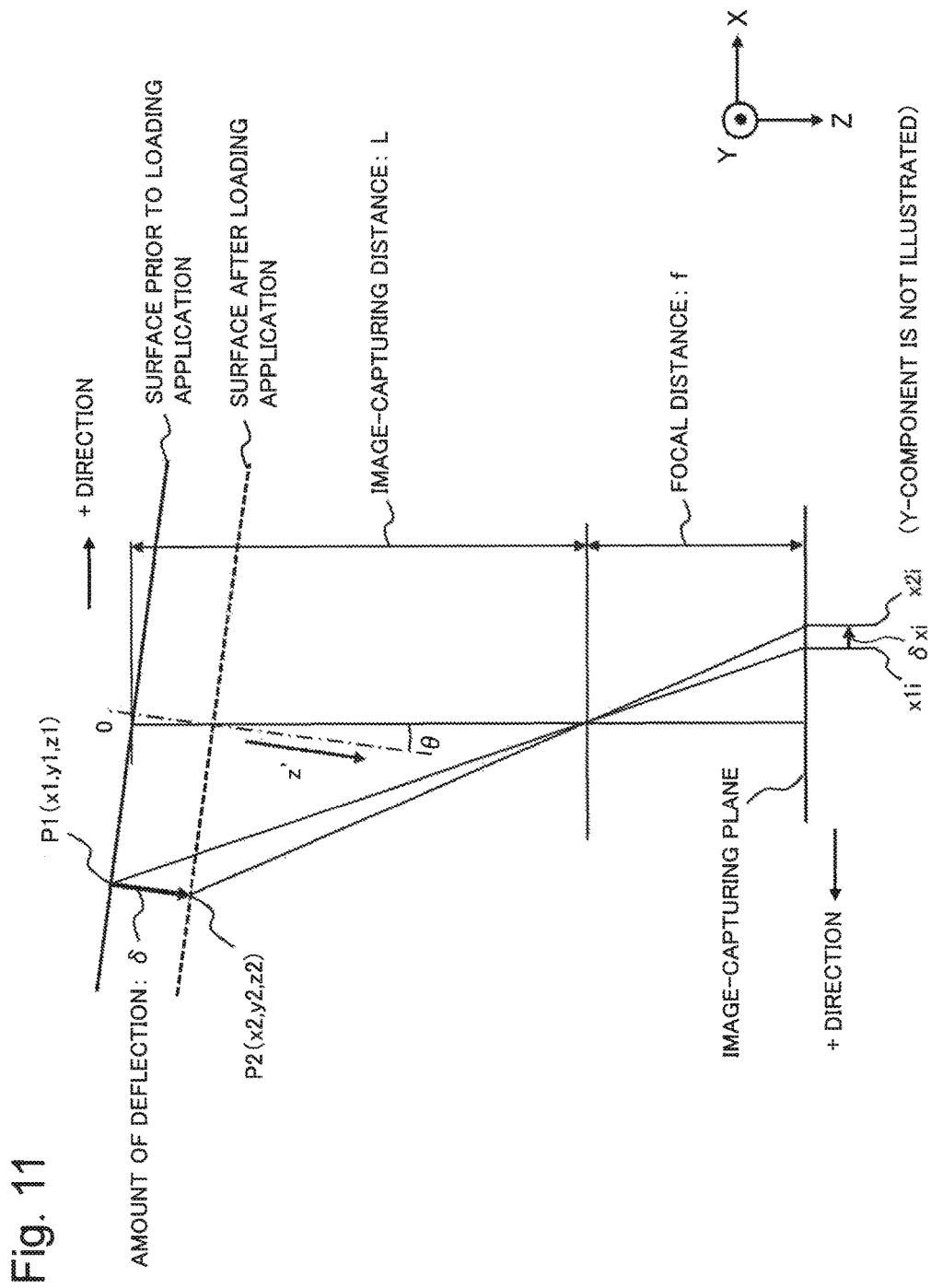
FIG. 11 is a diagram for explaining a calculation method of a correction amount when there is a tilt, in a correction amount calculation unit according to an example embodiment of the present invention.

FIG. 11 is a diagram for explaining an out-of-plane displacement when there is a tilt in the structure 12, in a calculation method of a correction amount adopted in the correction amount calculation unit 3. As illustrated in FIG. 11, when the vertical line on the surface of the structure 12 is rotated by θ with Y-axis serving as an axis, the relation between the coordinates with z-axis being the optical axis of the image-capturing unit 11 and the coordinates with the normal line of the structure surface being z' is expressed by Expression 13, Expression 14, and Expression 15.

[Math. 13]

$$x'=x^*\cos\theta + z^*\sin\theta \qquad \text{(Expression 13)}$$

[Math. 14]

$$y'=y \qquad \text{(Expression 14)}$$

[Math. 15]

$$z'=-x\cdot\sin\theta + z^*\cos\theta \qquad \text{(Expression 15)}$$

The X-Y coordinates of the image surface rotated by θ are mapped using Expression 16 and Expression 17.

[Math. 16]

$$X = \left(\frac{x' * f}{L - z'}\right) \quad \text{(Expression 16)}$$

[Math. 17]

$$Y = \left(\frac{y' * f}{L - z'}\right) \quad \text{(Expression 17)}$$

Consequently, the out-of-plane displacement $\delta x_i$ in X-direction and the out-of-plane displacement $\delta y_i$ in Y-direction, attributed to displacement from the coordinates P1(x1, y1, z1) to the coordinates P2(x2, y2, z2) by deflection of the structure 12 due to loading application, are expressed by Expression 18 and Expression 19, respectively (FIG. 11 does not illustrate the Y-component).

[Math. 18]

$$\delta xi = x2i - x1i = \left(\frac{x2 * f}{L - z2}\right) - \left(\frac{x1 * f}{L - z1}\right) \quad \text{(Expression 18)}$$

[Math. 19]

$$\delta yi = y2i - y1i = \left(\frac{y2 * f}{L - z2}\right) - \left(\frac{y1 * f}{L - z1}\right) \quad \text{(Expression 19)}$$

Therefore, if there is a tilt θ, the function R(θ) is obtained by substituting Expression 18 and Expression 19 into Expression 7. Here, when the tilt angle θ is unknown, the function R(θ) is used for each angle θ to obtain k(θ) at which the evaluation function E(k) in Expression 12 is minimized, by changing θ for example by 0.5° from 0° to 90°. Then, from among all the obtained k(θ), the angle at which the evaluation function E(k) is minimized is set to be the tilt angle. From the relation between "k" in this tilt angle and Expression 8, the amount of deflection δ is obtained. From the relation among the obtained tilt angle, the obtained amount of deflection δ, and Expressions 13, 14, 15, 16, 17, 18, and 19, the out-of-plane displacement vector $\delta i(\delta x_i, \delta y_i)$ can be estimated.

This result is input to the displacement correction unit 4 as an output from the correction amount calculation unit 3. The displacement correction unit 4 obtains the in-plane displacement vector $\Delta i(\Delta x_i, \Delta y_i)$ by subtracting the out-of-plane displacement vector $\delta i(\delta x_i, \delta y_i)$ from the measurement vector V(Vx, Vy). Here, the in-plane displacement of the structure can be obtained by calculating the projection onto the surface after loading application with respect to the in-plane displacement vector $\Delta i(\Delta x_i, \Delta y_i)$ using Expressions 13, 14, 15, 16, and 17.

FIG. 11 deals with a case in which, where Y-axis serves as an axis, the normal line of the surface of the structure 12 is rotated by θ with respect to the optical axis in the center of the image-capturing direction of the image-capturing unit 11. However, correction is also possible in cases where X-axis or Z-axis serves as an axis.

The in-plane displacement on the structure surface, being the output of the displacement correction unit 4, is replaced with the strain on the structure surface in the differential displacement calculation unit 5. By multiplying the strain on the structure surface by a Young's modulus, the stress will result. Accordingly, the stress field on the structure surface is obtained. The displacement information obtained by the displacement correction unit 4 and the strain information obtained by the differential displacement calculation unit 5 are input to the abnormality determination unit 6.

For the purpose of identifying the type and location of a defect for the displacement information obtained by the displacement correction unit 4 and the strain information obtained by the differential displacement calculation unit 5, the abnormality determination unit 6 includes, in advance, a threshold value for determining a defect, and patterns of a characteristic displacement and strain for the type of defect, in the two-dimensional spatial distribution information analysis unit 7 and the temporal change information analysis unit 8. The two-dimensional spatial distribution information analysis unit 7 and the temporal change information analysis unit 8 thereby determine the sound status or a defect such as a crack, a separation, and an internal cavity, as illustrated in FIG. 4A to FIG. 4D, by comparing the displacement information or the strain information with the threshold value or by means of pattern matching with the pattern.

FIG. 10A illustrates an example of an in-plane displacement on a surface of a structure in X-direction due to loading application when there is a crack along Y-direction. It can be understood that a steep and discontinuous in-plane displacement of 20 μm is generated in the cracked portion. Such a sudden displacement will not be generated in a sound status without defects. Therefore, by providing a threshold value for a size of a discontinuous displacement in advance, a crack can be detected when a displacement exceeding this is confirmed.

FIG. 12A and FIG. 12B illustrate a distribution of a stress field around a cracked portion calculated by the differential displacement calculation unit 5 when there is a crack along Y-direction. As illustrated in FIG. 12A, the direction of the stress will be bent by the crack. Therefore, even when there is a tensile stress exerted on both ends of the structure in X-direction in FIG. 12A, a Y-direction component will be generated in the direction of the stress in the vicinity of the crack as illustrated in FIG. 12B. Therefore, a crack can also be detected by detecting whether there is this Y-direction component. Note that a distribution of such a stress field around a crack is known as a stress intensity factor in an elastic body which exhibits a linear response, and thus such information can also be used.

Figure 13A:
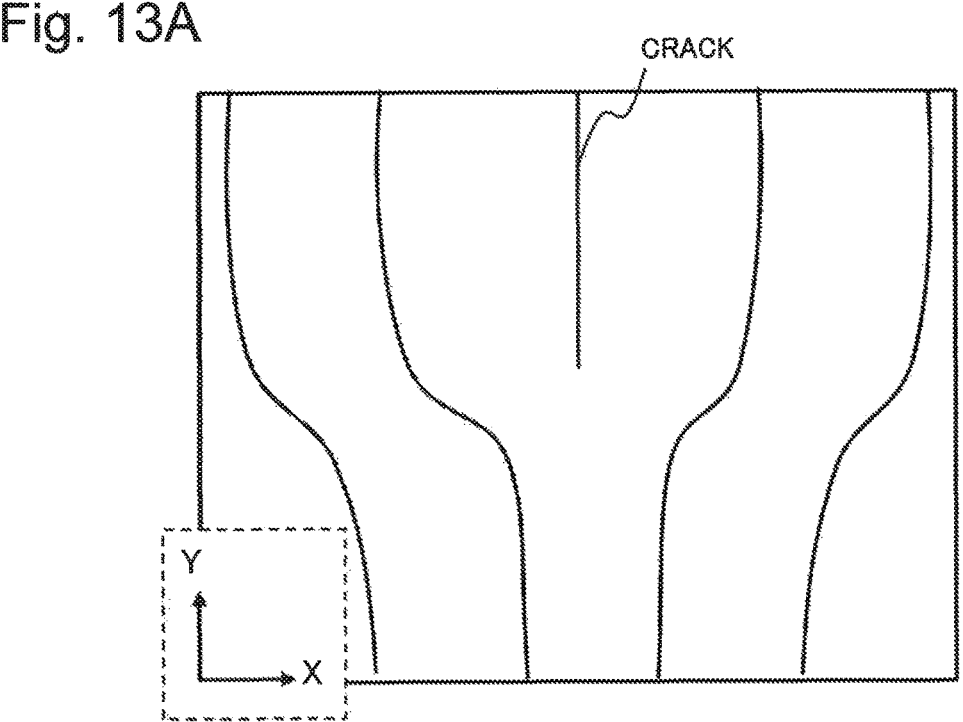
FIG. 13A is a diagram illustrating an example of a two-dimensional distribution (X-direction) of a displacement amount around a crack (when the crack is shallow).
Figure 13B:
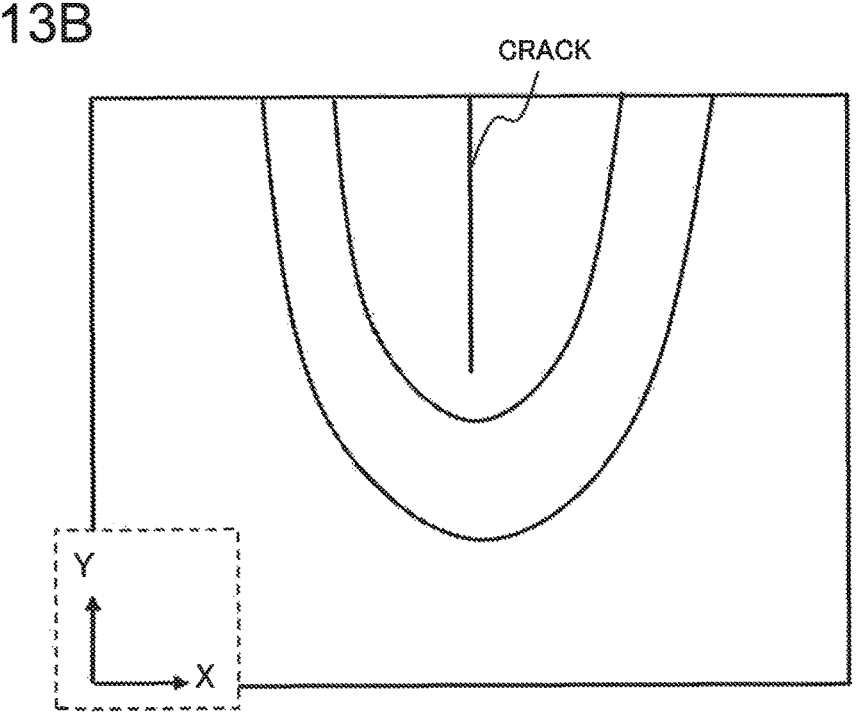
FIG. 13B is a diagram illustrating an example of a two-dimensional distribution (Y-direction) of a displacement amount around a crack (when the crack is shallow).

FIG. 13A to FIG. 13D illustrate an example of a two-dimensional displacement distribution of a displacement amount around a crack. FIG. 13A and FIG. 13B are a contour of a displacement amount in a direction horizontal (X-direction) in FIG. 4B and in a direction vertical (Y-direction) to the paper in which the drawing is drawn in FIG. 4B. As illustrated in FIG. 13A, in X-direction, the contour of the displacement amount is less dense around a crack than in the area without cracks. This corresponds to the portion of a moderate displacement outside the steep displacement in the cracked portion illustrated in FIG. 10A. The displacement in this portion is more moderate than the displacement without cracks.

As illustrated in FIG. 13B, in Y-direction, a Y-direction component of a displacement is generated in an area around the cracked portion. This corresponds to the Y-direction component in the stress field (strain) illustrated in FIG. 12B.

Figure 13C:
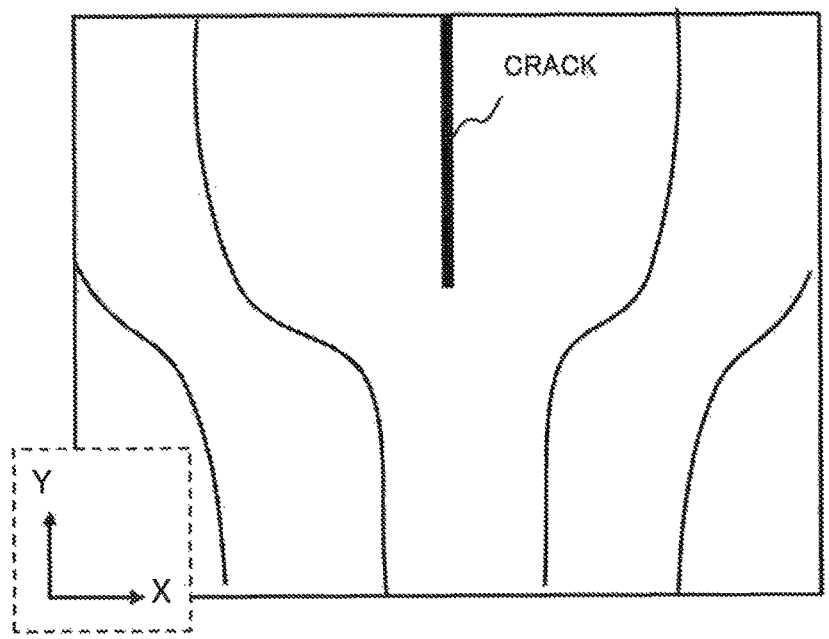
FIG. 13C is a diagram illustrating an example of a two-dimensional distribution (X-direction) of a displacement amount around a crack (when the crack is deep).
Figure 13D:
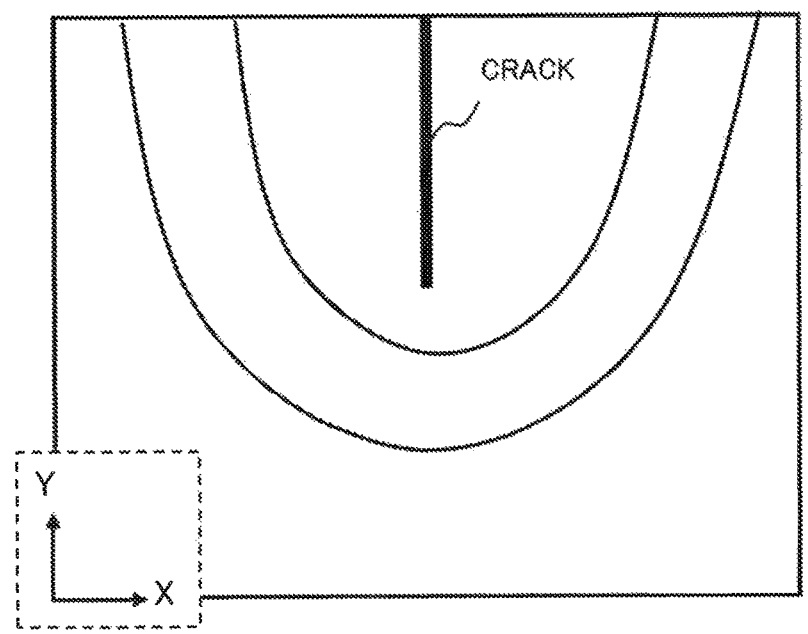
FIG. 13D is a diagram illustrating an example of a two-dimensional distribution (Y-direction) of a displacement amount around a crack (when the crack is deep).

FIG. 13C and FIG. 13D each illustrate a case in which a crack is deeper than in the cases of FIG. 13A and FIG. 13B. In these cases, the contour of the displacement amount is less dense in an area around a crack in each of X-direction and Y-direction. It is also possible to know the depth of a crack, from this density information.

The determination of a crack as described above is performed in the two-dimensional spatial distribution information analysis unit 7 in the abnormality determination unit 6 in FIG. 2.

When there is a crack, as the crack is wider open, the displacement amount will increase sharply in the cracked portion, as illustrated in FIG. 10A. Therefore, by preparing each threshold value for the displacement amounts per unit length in X-direction or Y-direction, it is possible to expect a crack at a location where the displacement amount that exceeds the threshold value is detected.

In addition, the strain in X-direction becomes rapidly large at the cracked portion. For this reason, by preparing a threshold value for the strain value in X-direction, it is possible to expect a crack at a location where a strain that exceeds the threshold value is detected.

Furthermore, as illustrated in FIG. 12A and FIG. 12B, when there is a crack, a strain in Y-direction is caused. Therefore, by preparing a threshold value for the strain value in Y-direction, it is possible to expect a crack at a location where a strain that exceeds the threshold value is detected.

Each threshold value described above can be set by a simulation using a size or a material similar to those of the structure, an experiment using a reduced-size model, and the like. The threshold value can also be set by measuring the actual structure for a long period of time and accumulating the data.

The above-described determination can also be performed by pattern matching processing as described below, not limited to the above-described numerical comparison.

FIG. 14A to FIG. 14C are a diagram illustrating pattern matching processing of a displacement distribution by the two-dimensional spatial distribution information analysis unit 7. By using the displacement correction unit 4 and the differential displacement calculation unit 5, the displacement amount can be represented as a displacement diagram on the X-Y plane, as illustrated in FIG. 13A to FIG. 13D. As illustrated in FIG. 14A, the two-dimensional spatial distribution information analysis unit 7 rotates, or scales up or down the pattern in X-direction of the displacement around the crack having been stored in advance, subjects the same to pattern matching with the displacement distribution diagram obtained in the displacement correction unit 4, to determine the direction and depth of the crack. Here, the pattern in X-direction of the displacement around the crack having been stored in advance may be created in advance by simulation or the like, for each depth or width of a crack.

In addition, as illustrated in FIG. 14B, the two-dimensional spatial distribution information analysis unit 7 rotates, or scales up or down the pattern in Y-direction of the displacement around the crack having been stored in advance, subjects the same to pattern matching with the displacement distribution diagram obtained in the displacement correction unit 4, to determine the direction and depth of the crack. Here, the pattern in Y-direction of the displacement around the crack having been stored in advance may be created in advance by simulation or the like, for each depth or width of a crack.

In addition, as illustrated in FIG. 14C, the two-dimensional spatial distribution information analysis unit 7 rotates, or scales up or down the pattern of the differential vector field of the displacement around the crack having been stored in advance, subjects the same to pattern matching with the differential vector field (corresponding to a stress field) obtained in differential displacement calculation unit 5, to determine the direction and depth of the crack. Here, the pattern of the differential vector field of the displacement around the crack having been stored in advance may be created in advance by simulation or the like, for each depth or width of a crack.

A correlation operation is used in the pattern matching. The pattern matching may be performed using various other statistical operational approaches.

So far, the cases in which the structure 12 has a crack have been described. As follows, the cases in which the structure 12 has an internal cavity and the cases in which the structure 12 has a separation are described.

Figure 15A:
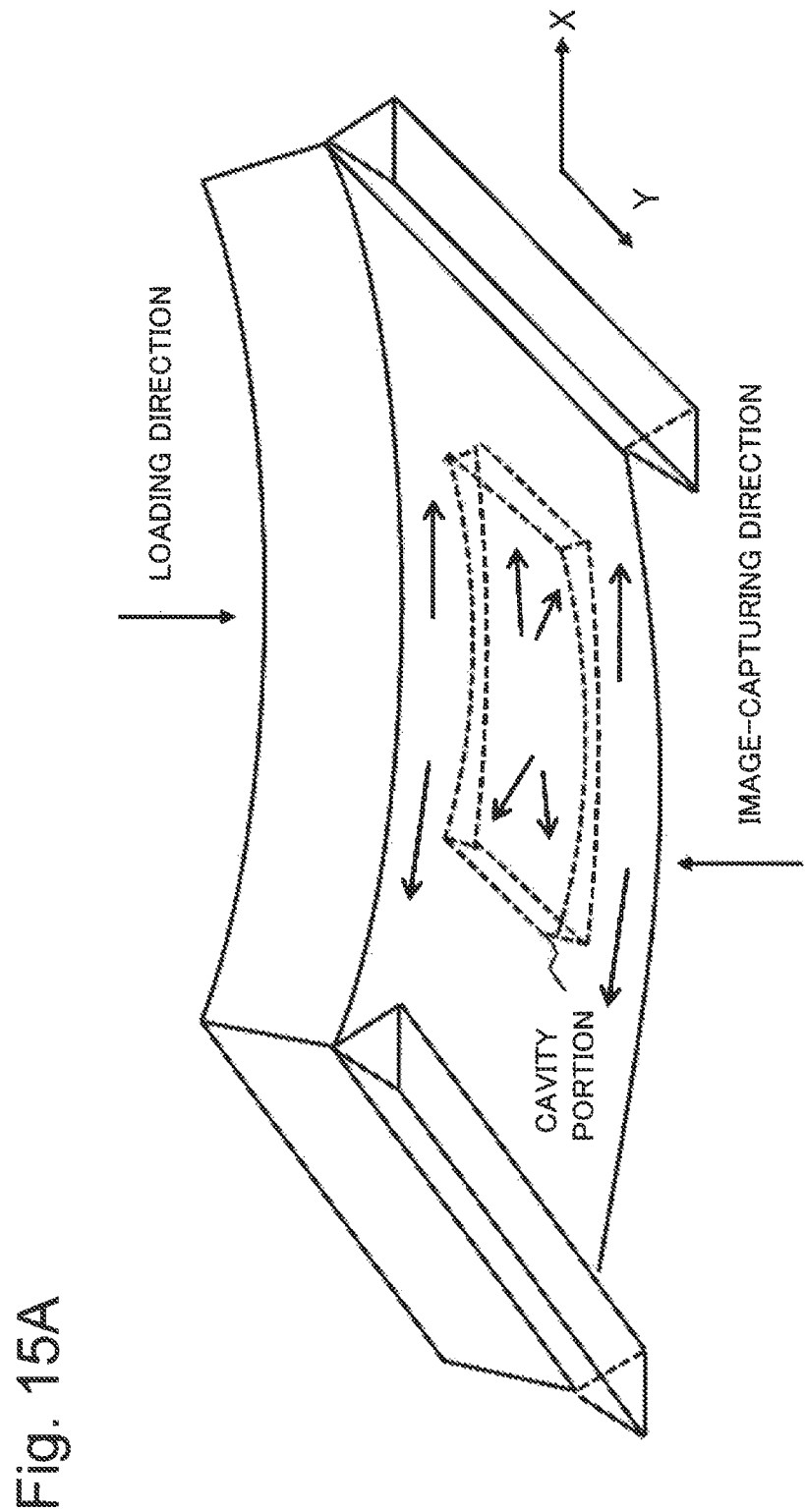
FIG. 15A is a perspective view illustrating a two-dimensional distribution of a stress on a surface viewed along the image-capturing direction when there is an internal cavity.

FIG. 15A and FIG. 15B illustrate a two-dimensional distribution of a stress on a surface viewed along the image-capturing direction when there is an internal cavity as illustrated in FIG. 4D, where FIG. 15A is a perspective view and FIG. 15B is a plan view. As illustrated in FIG. 15B, loading causes a stress exerted in X-direction in the drawing. However, in the cavity portion, the stress field is bent, to causes the stress to contain a component in Y-direction as illustrated in the drawing.

Figure 16A:
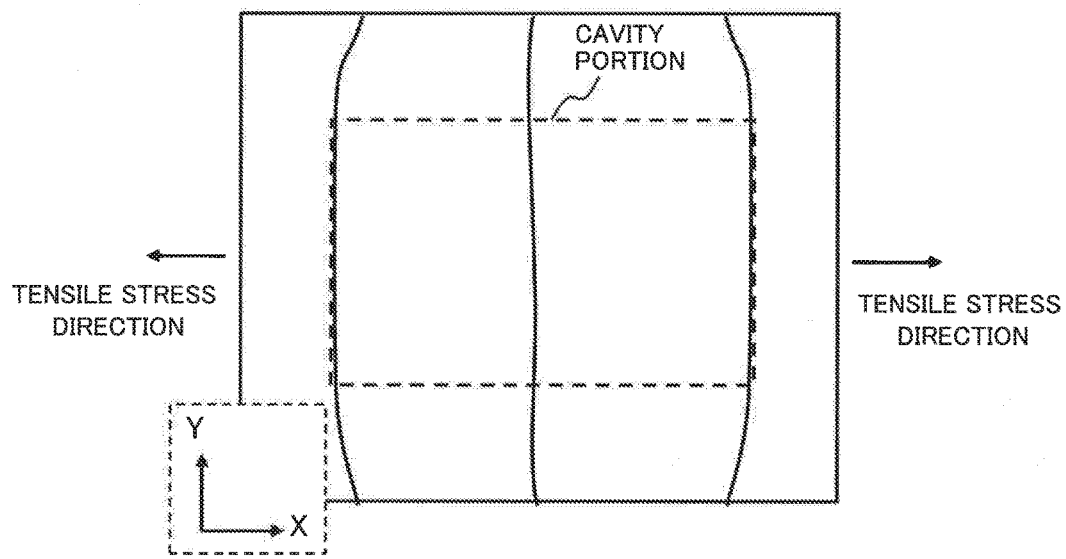
FIG. 16A is a diagram illustrating a contour (X-component) of a displacement of a surface viewed along the image-capturing direction when there is an internal cavity.
Figure 16B:
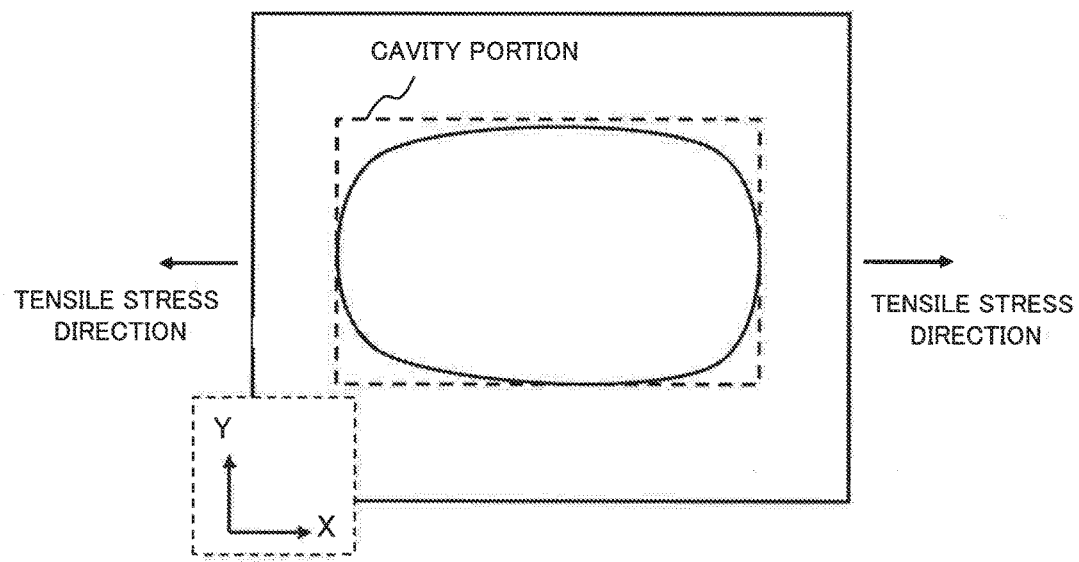
FIG. 16B is a diagram illustrating a contour (Y-component) of a displacement of a surface viewed along the image-capturing direction when there is an internal cavity.
Figure 16C:
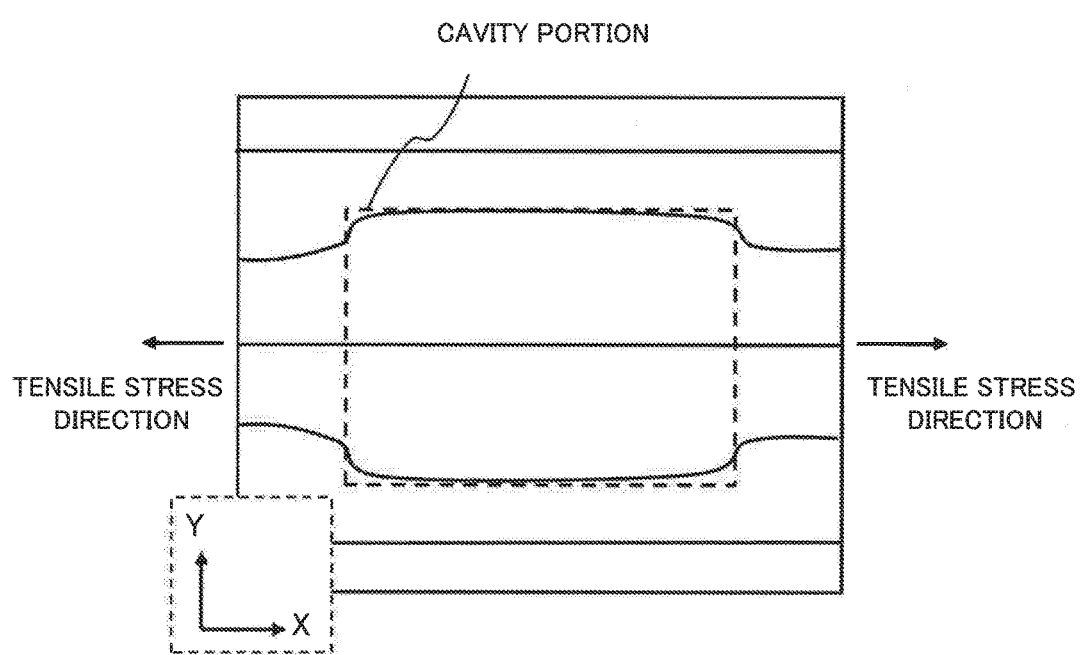
FIG. 16C is a diagram illustrating a stress field on a surface viewed along the image-capturing direction when there is an internal cavity.

FIG. 16A to FIG. 16C are diagrams illustrating a contour and a stress field of a displacement of a surface viewed along the image-capturing direction when there is an internal cavity. FIG. 16A illustrates a contour of an X-component of the displacement, FIG. 16B illustrates a contour of a Y-component of the displacement, and FIG. 16C illustrates a stress field.

As illustrated in the description about FIG. 4D, a strain amount is small in a cavity portion. Therefore, the density of the contour of the X-component of the displacement illustrated in FIG. 16A is small. The contour of the Y-component of the displacement illustrated in FIG. 16B takes a form of a closed curve. Further, the stress field, which is a differential of the displacement and is illustrated in FIG. 16C, is bent at the cavity portion. The effect of the stress field on the surface gets more noticeable when the cavity portion is closer to the surface. Therefore, the depth of a cavity portion from the surface can also be estimated from how the stress field is bent.

Here, just as when a crack is determined, by replacing FIG. 14A with FIG. 16A, FIG. 14B with FIG. 16B, and FIG. 14C with FIG. 16C, with respect to the pattern in X-direction of the displacement around the cavity, the pattern in Y-direction of the displacement around the cavity, and the differential vector field (corresponding to a stress field), which have been stored in advance in the two-dimensional spatial distribution information analysis unit 7, the status determination of the location and depth of the internal cavity can be performed. The pattern matching uses a correlation operation. The pattern matching may be performed using various other statistical operational approaches.

In case of internal cavity, too, by preparing a threshold value for the displacement amount in Y-direction and the strain in Y-direction based on the characteristics of these displacement amount and strain, it is possible to expect an internal cavity when the threshold value is exceeded.

Figure 17A:
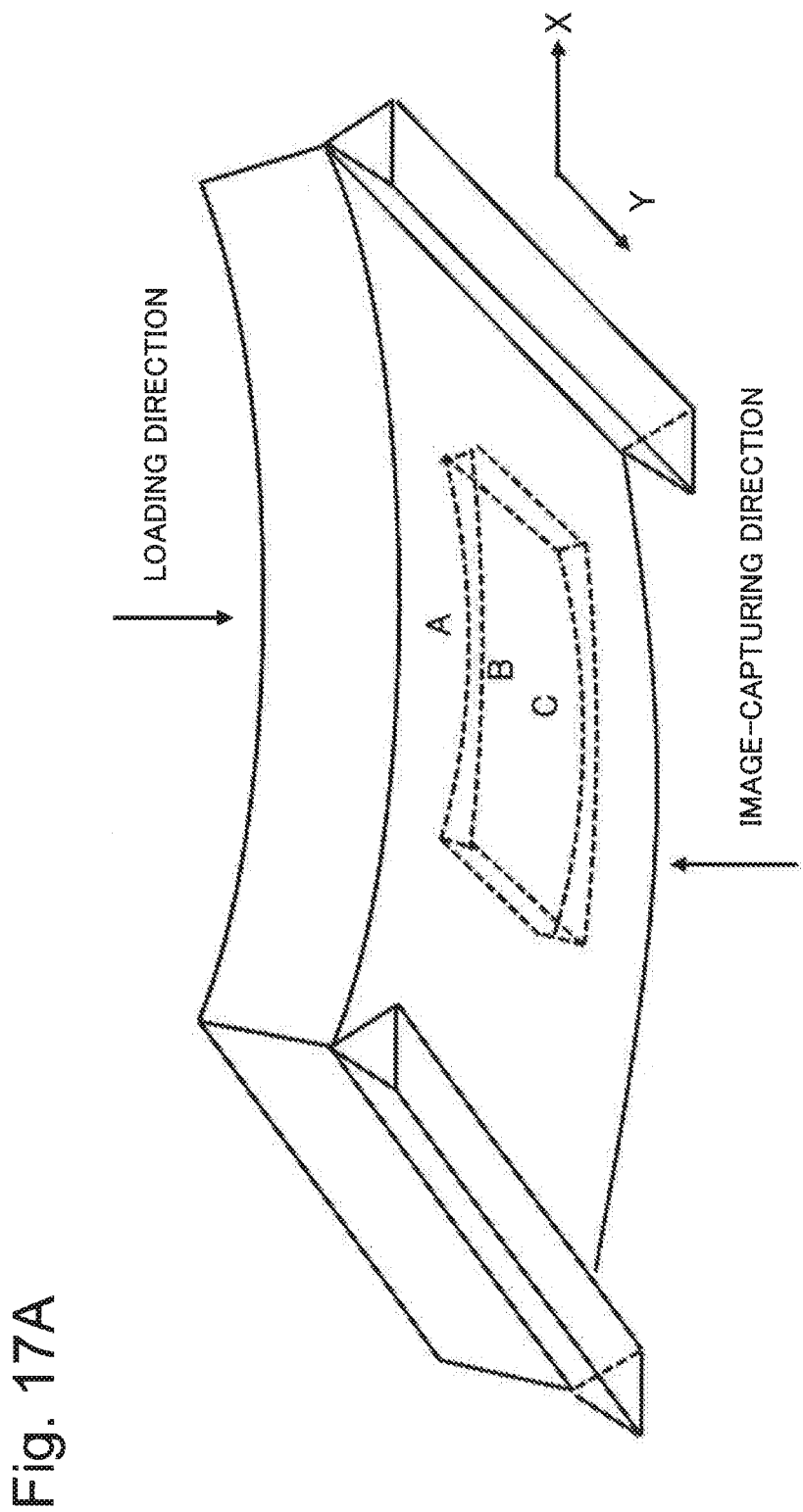
FIG. 17A is a diagram for explaining a response when an impulse stimulation is provided on a structure when there is an internal cavity (illustrating a location ABC at which a response is obtained).
Figure 17B:
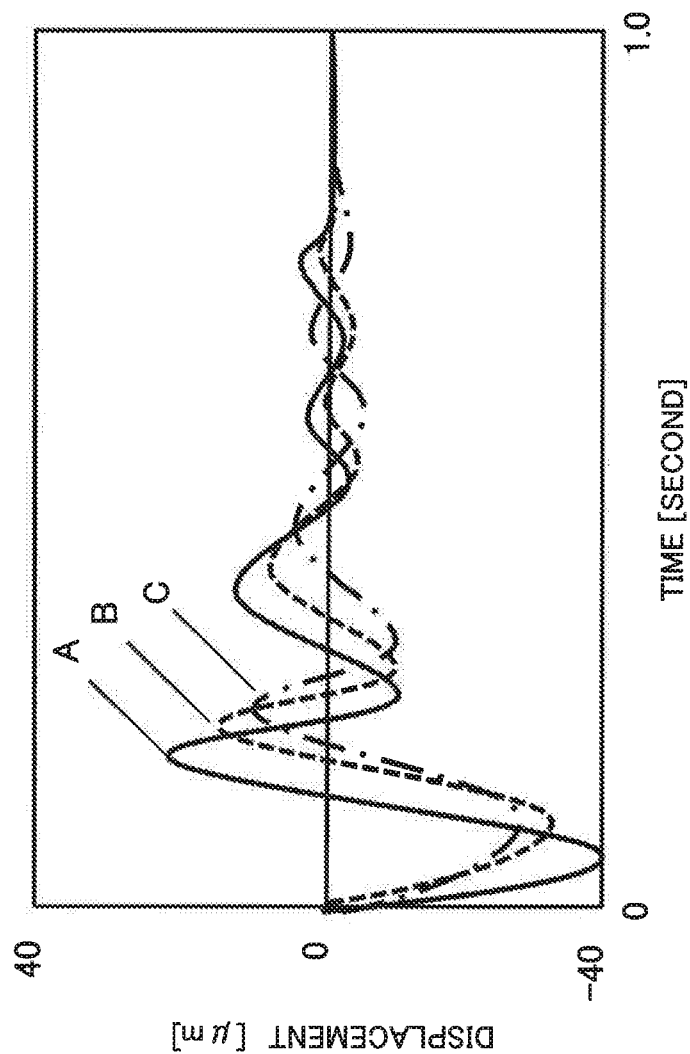
FIG. 17B is a diagram for explaining a response when an impulse stimulation is provided on a structure when there is an internal cavity (illustrating a location ABC at which a response is obtained).

FIG. 17A and FIG. 17B are diagrams for explaining a response when short-term loading (referred to as "impulse stimulation") is applied onto a structure having an internal cavity. The impulse stimulation can be applied on a location to be applied with loading, for example. FIG. 17B illustrates a time response of displacement at each point A, B, C on a surface illustrated in FIG. 17A in response to this impulse stimulation. At point A with no internal cavity, the stress is conveyed fast, and the amplitude of displacement is great. At point C, however, since the stress is not conveyed within the internal cavity but is conveyed from around the cavity, the stress is conveyed slowly and the amplitude of the displacement is small. At point B, which is halfway through point A and point C, the stress conveyance time and amplitude are the values between those of point A and point C. Therefore, when the displacement distribution within the plane when the structure is viewed along the image-capturing direction is subject to frequency analysis in the temporal change information analysis unit 8 in the abnormality determination unit 6, the area of the internal cavity can be identified, from the amplitude and the phase near the resonant frequency. An internal cavity may be determined by the shift in the resonant frequency.

Note that even when loading is applied for a long period of time, in the initial stage of loading application, the fluctuation in displacement, which corresponds to FIG. 17B, will be confirmed. In this case, however, the value at which the displacement converges is not zero, but is a value balanced with loading. Therefore, even when loading is applied for a long period of time, the temporal change information analysis unit 8 can still identify the area of the internal cavity.

The temporal change information analysis unit 8 performs the above-described displacement time response processing by frequency analysis using fast Fourier transform. The frequency analysis may be performed by various types of frequency analysis approaches, such as wavelet transform.

Figure 18A:
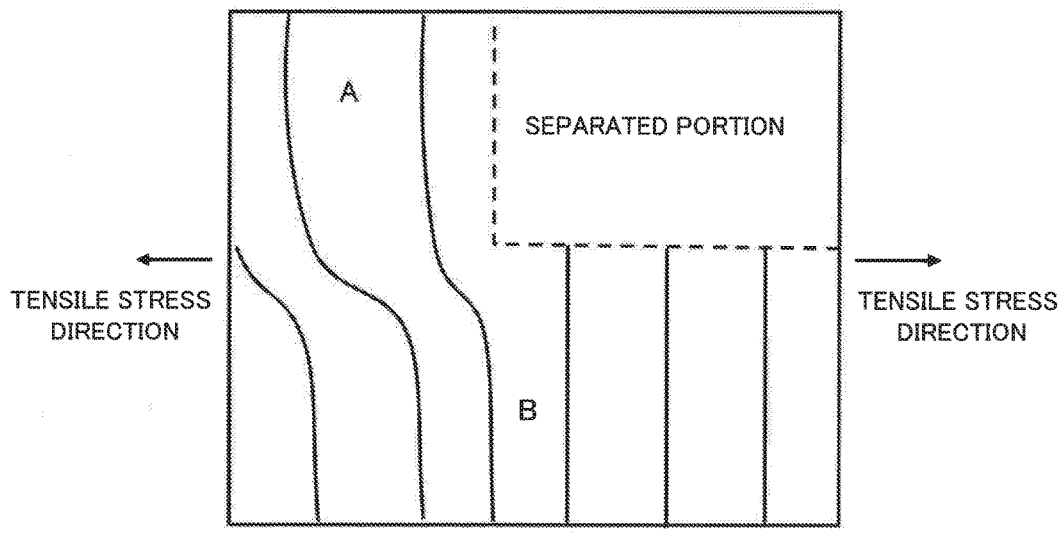
FIG. 18A is a diagram illustrating a contour (X-component) of a displacement of a surface viewed along the image-capturing direction when there is a separation.
Figure 18B:
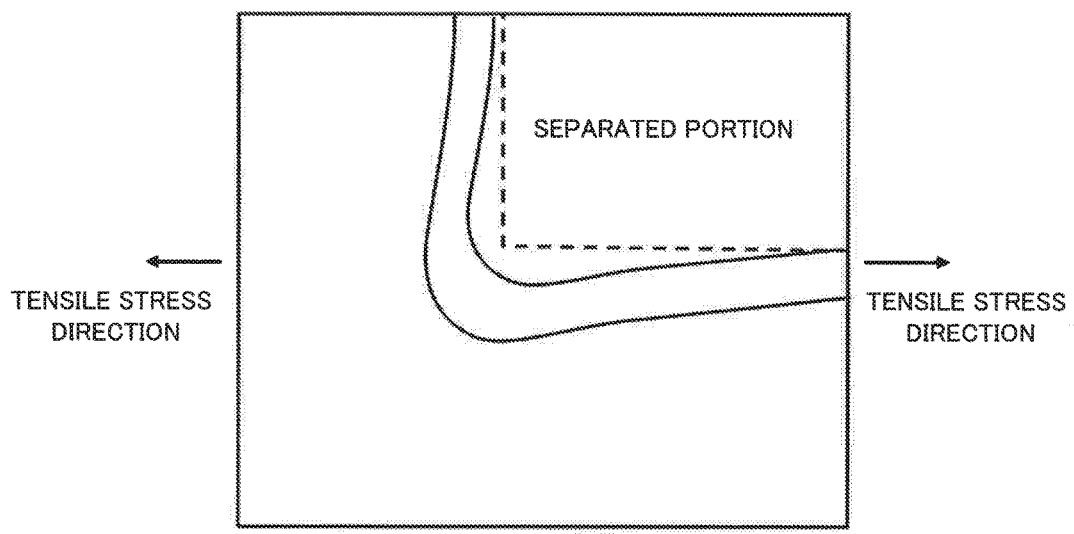
FIG. 18B is a diagram illustrating a contour (Y-component) of a displacement of a surface viewed along the image-capturing direction when there is a separation.
Figure 18C:
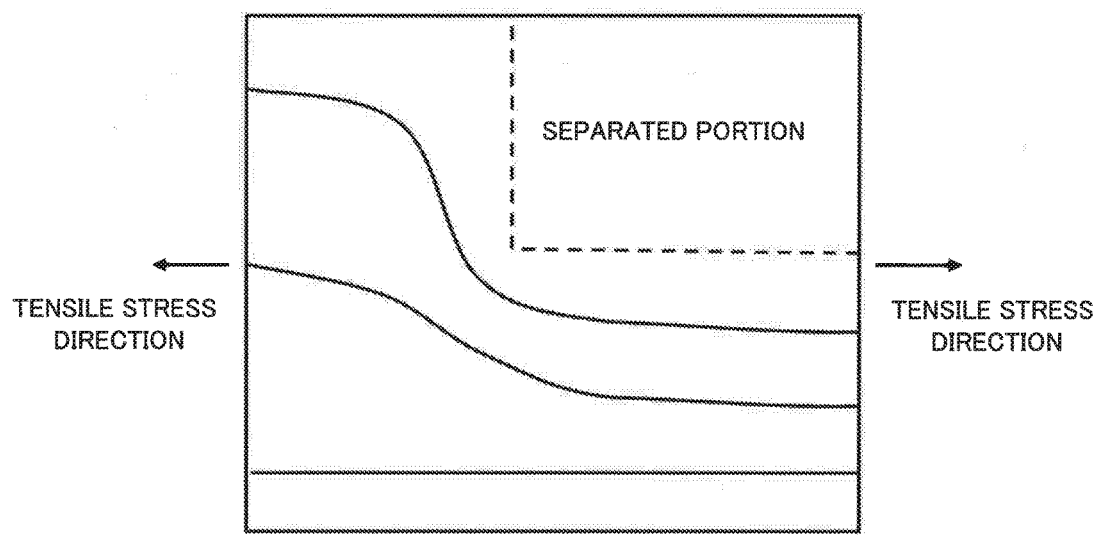
FIG. 18C is a diagram illustrating a stress field on a surface viewed along the image-capturing direction when there is a separation.

FIG. 18A to FIG. 18C are diagrams illustrating a contour and a stress field of a displacement of a surface viewed along the image-capturing direction when there is a separation. FIG. 18A illustrates a contour of an X-component of the displacement, FIG. 18B illustrates a contour of a Y-component of the displacement, and FIG. 18C illustrates a stress field.

As illustrated in FIG. 4C, when there is a separation, the outer appearance similar to that of a crack is observed when viewed from the lower surface of the beam-like structure. However, no stress is conveyed from the separated portion to the portion above the separated portion; therefore, at the separated portion, the displacement after loading compared to before loading only moves in parallel in a certain amount and in a certain direction, and no strain, being its spatial differential value, will be caused.

FIG. 18A illustrates a contour of an X-component of a displacement. The separated portion does not have a contour because there is no strain and moves in a certain direction. Using this characteristic, the abnormality determination unit 6 determines that there is a separation. The portion corresponding to point A in the drawing is a cleavage due to a separation, at which a stress is hardly conveyed, and has a less dense contour than in point B which is a sound portion. The abnormality determination unit 6 may use this characteristic to distinguish between the separated portion and the sound portion.

FIG. 18B illustrates a contour of a Y-component of a displacement. A Y-direction displacement is caused at a portion outside the separated portion. Using this characteristic, the abnormality determination unit 6 can determine that there is a separation. In addition, the stress field that is a differential of the displacement illustrated in FIG. 18C takes either 0 or a value near 0 at the separated portion. The abnormality determination unit 6 may use this characteristic to determine that there is a separation.

Here, just as when the depth of a crack is determined, by replacing FIG. 14A with FIG. 18A, FIG. 14B with FIG. 18B, and FIG. 14C with FIG. 18C, with respect to the pattern in X-direction of the displacement around the separation, the pattern in Y-direction of the displacement around the cavity, and the differential vector field (corresponding to a stress field), which have been stored in advance in the two-dimensional spatial distribution information analysis unit 7, the location of the separation can be determined. The pattern matching uses a correlation operation. The pattern matching may be performed using various other statistical operational approaches.

Figure 19:
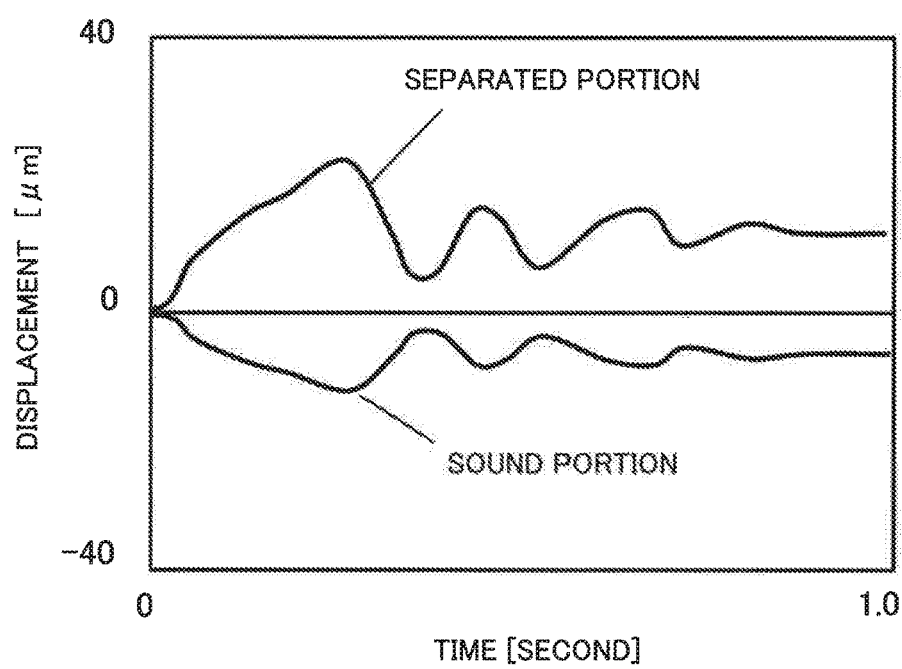
FIG. 19 is a diagram for explaining a time response of a displacement when an impulse stimulation is provided on a structure when there is a separation.

FIG. 19 is a diagram illustrating a time response when the structure having a separation is subject to an impulse stimulation. In the time response, the separated portion has a displacement that is reverse to that of the sound portion; that is, the separated portion takes a waveform whose phase is 180° different from the sound portion. In addition, the separated portion has a great amplitude because of being light. When the displacement distribution within the plane when the structure is viewed along the image-capturing direction is subject to frequency analysis in the temporal change information analysis unit 8, the separated portion can be identified based on the amplitude and the phase. Moreover, because of being separated away from the entire structure, a separated portion likely include a frequency component different from that of the entire structure. Therefore, a separated portion may be determined by the shift in the resonant frequency.

In the above processing, the temporal change information analysis unit 8 performs frequency analysis using fast Fourier transform. The frequency analysis may be performed by various types of frequency analysis approaches, such as wavelet transform.

Figure 20:
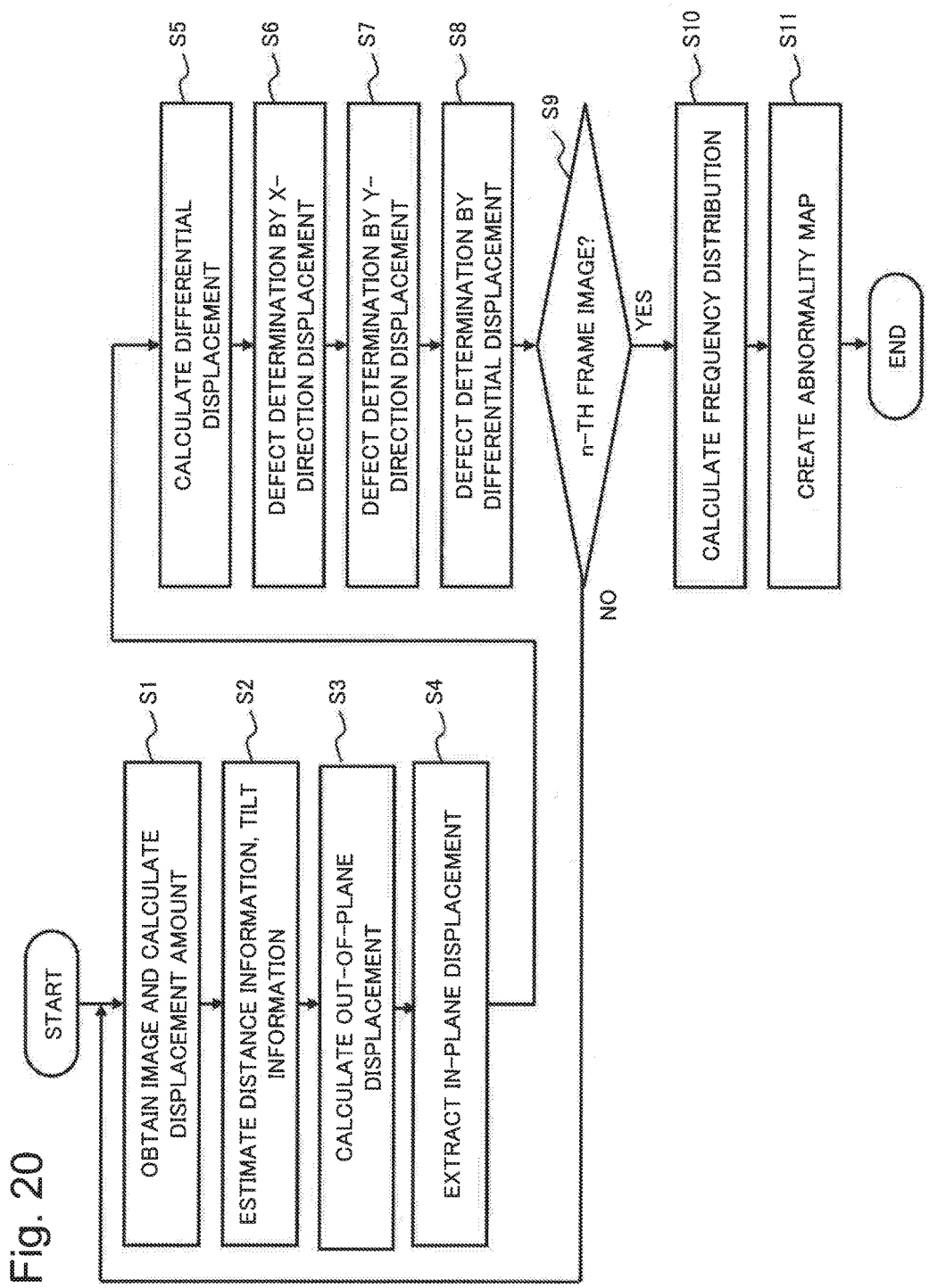
FIG. 20 is a flowchart illustrating a status determination method in a status determination device according to an example embodiment of the present invention.

FIG. 20 is a flowchart illustrating a status determination method of the status determination device 1 as illustrated in FIG. 2.

In Step S1, the displacement calculation unit 2 in the status determination device 1 takes in a frame image before loading application which serves as a reference in calculating a displacement amount after the loading application, compared to before the loading application, for the time-series images of the surface of the structure 12 before and after the loading application which have been captured by the image-capturing unit 11, and further takes in frame images after the loading application in time series.

The displacement calculation unit 2 calculates a displacement amounts in X, Y-directions of the image after the loading application with respect to the image before the loading application which serves as a reference. A displacement distribution diagram (a contour of the displacement amount) may also be drawn in which the two-dimensional distribution of the calculated displacement amount is displayed on the X-Y plane. The displacement calculation unit 2 inputs the calculated displacement amount or the displacement distribution diagram, to the correction amount calculation unit 3 and the displacement correction unit 4.

In Step S2, from the two-dimensional spatial distribution of the displacement of the time-series images calculated by the displacement calculation unit 2, the correction amount calculation unit 3 estimates distance information representing a distance in which the surface of the structure 12 has moved in its normal direction by deflection of the structure 12 due to loading or the like, as well as tilt information representing an angle formed by the optical axis of the image-capturing unit 11 and the normal line of the surface of the structure 12.

In Step S3, the correction amount calculation unit 3 calculates an out-of-plane displacement from the distance information and the tilt information.

In Step S4, the displacement correction unit 4 extracts the in-plane displacement by subtracting the out-of-plane displacement obtained in the correction amount calculation unit 3, from the displacement amount obtained in the displacement calculation unit 2. That is, the displacement correction unit 4 calculates the in-plane displacement in the X-Y direction of the surface of the structure 12 after loading application, with respect to before the loading application which serves as a reference. A displacement distribution diagram (a contour of the displacement amount) may also be drawn in which the two-dimensional distribution of the calculated in-plane displacement is displayed on the X-Y plane. The displacement correction unit 4 inputs the calculated result, to the differential displacement calculation unit 5 and the abnormality determination unit 6.

In Step S5, the differential displacement calculation unit 5 subjects the in-plane displacement or the displacement distribution diagram input by the displacement correction unit 4 to spatial differential processing, to calculate a differential displacement amount (stress value) or a differential displacement distribution diagram (stress field). The differential displacement calculation unit 5 inputs the calculated result to the abnormality determination unit 6.

The following-described Step S6, Step S7, and Step S8 are steps in which the two-dimensional spatial distribution information analysis unit 7 of the abnormality determination unit 6 determines a crack, a separation, and an internal cavity, being a defect of a structure. As a determination method, the pattern matching method and the method by way of a threshold value, having been described above, are taken as an example.

In Step S6, the two-dimensional spatial distribution information analysis unit 7 of the abnormality determination unit 6 determines the status of a crack, a separation, or an internal cavity, from the displacement amount in X-direction or the displacement distribution diagram having been input.

First, the determination method by way of pattern matching is described. The two-dimensional spatial distribution information analysis unit 7 includes, as a database, a displacement distribution pattern created in advance corresponding to a width, a depth, or the like of a crack, an internal cavity, or a separation as illustrated in FIG. 14A, FIG. 16A, and FIG. 18A. The two-dimensional spatial distribution information analysis unit 7 performs pattern matching, by rotating or scaling up or down these displacement distribution patterns with respect to the displacement distribution diagram in X-direction input from the displacement correction unit 4, thereby determining the location or type of the defect on the X-Y plane.

Next, the determining method by way of a threshold value of a displacement amount is described. The two-dimensional spatial distribution information analysis unit 7 determines continuity of the displacement amount, for example, based on the displacement amount in X-direction having been input. That is, as illustrated in FIG. 10A, whether there is continuity is determined based on whether there is a sudden change of a threshold value or above in the displacement amount. When there is a sudden change suggesting no continuity in any part on the X-Y plane, the two-dimensional spatial distribution information analysis unit 7 determines that there is a possibility of a crack or a separation existing in that part, and sets a discontinuity flag Dis C(x, y, t) to 1, and records, as numerical value information, the displacement amount data for the portion subject to the sudden change. Here, "t" indicates a time of the frame image taken in Step S1 on the time-series images.

The abnormality determination unit 6 inputs, to the abnormality map creation unit 9, information on the defect determined by the pattern matching, or the discontinuity flag Dis C(x, y, t) or the numerical value information determined by the threshold value of the displacement amount.

In Step S7, the two-dimensional spatial distribution information analysis unit 7 of the abnormality determination unit 6 determines the status of a crack, a separation, or an internal cavity, from the displacement amount in Y-direction or the displacement distribution diagram having been input.

First, the determination method by way of pattern matching is described. The two-dimensional spatial distribution information analysis unit 7 includes, as a database, a displacement distribution pattern created in advance corresponding to a width, a depth, or the like of a crack, an internal cavity, or a separation as illustrated in FIG. 14B, FIG. 16B, and FIG. 18B. The two-dimensional spatial distribution information analysis unit 7 performs pattern matching, by rotating or scaling up or down these displacement distribution patterns with respect to the displacement distribution diagram in Y-direction input from the displacement correction unit 4, thereby determining the location or type of the defect on the X-Y plane.

Next, the determining method by way of a threshold value of a displacement amount is described. When there is a defect such as a crack, a separation, or an internal cavity, a displacement amount in Y-direction is also generated. Therefore, when detecting a displacement amount which is greater than a pre-set threshold value, the two-dimensional spatial distribution information analysis unit 7 determines that there is a defect in that part, and sets an orthogonal flag ortho(x, y, t) to 1, and records, as numerical value information, the displacement amount data for the portion for which a displacement amount which is greater than the pre-set threshold value has been detected.

The abnormality determination unit 6 inputs, to the abnormality map creation unit 9, the information on the defect determined by pattern matching, or the orthogonal flag ortho(x, y, t) or the numerical value information determined by the displacement amount.

In Step S8, the two-dimensional spatial distribution information analysis unit 7 of the abnormality determination unit 6 determines the status of a crack, a separation, or an internal cavity, from the differential displacement amount (stress value) or the differential displacement distribution diagram (stress field) having been input.

First, the determination method by way of pattern matching is described. The two-dimensional spatial distribution information analysis unit 7 includes, as a database, a displacement distribution pattern created in advance corresponding to a width, a depth, or the like of a crack, an internal cavity, or a separation as illustrated in FIG. 14C, FIG. 16C, and FIG. 18C. The two-dimensional spatial distribution information analysis unit 7 performs pattern matching, by rotating or scaling up or down these displacement distribution patterns with respect to the differential displacement distribution diagram input from the differential displacement calculation unit 5, thereby determining the location or type of the defect on the X-Y plane.

Next, the determining method by way of a threshold value of a differential displacement amount is described. In cracked portions, the strain in X-direction, for example, increases sharply because its displacement differential value diverges. For this reason, by providing in advance a threshold value for strain value, it is possible to determine that there is a crack in a portion in which a strain exceeding the threshold value is detected. The two-dimensional spatial distribution information analysis unit 7 determines that there is a crack in the portion based on the input differential displacement amount, and sets the differential value flag Diff(x, y, t) to 1, and records, as numerical value information, the differential displacement amount data for the defective portion.

The abnormality determination unit 6 inputs, to the abnormality map creation unit 9, information on the defect determined by the pattern matching, or the differential value flag Diff(x, y, t) or the numerical value information determined by the differential displacement amount.

In Step S9, the displacement calculation unit 2 determines whether the processing of each frame image of the time-series images is completed. That is, if there are n frames in the time-series images, the displacement calculation unit 2 determines whether the processing of n-th frame is completed. If the processing of the n frame images has not been completed (NO), the processing is repeated from Step S1. This is repeated until the n frame images are processed. Note that "n" is not limited to the total number of frames, and may be set to any number. When the processing of the n frame images has been completed (YES), the processing proceeds to Step S10.

In Step S10, the temporal change information analysis unit 8 of the abnormality determination unit 6 analyzes the time response of the displacement as illustrated in FIG. 17B or FIG. 19, based on the time-series displacement amount or the displacement distribution diagram corresponding to the n frame images. That is, from n displacement distribution diagrams I(x, y, n), a time frequency distribution (time frequency is denoted as "f") is calculated as a amplitude A(x, y, f), and a phase P(x, y, f). When the time frequency distribution is characterized to have different phases depending on locations as illustrated in FIG. 17B, the temporal change information analysis unit 8 determines that there is an internal cavity in a portion that undergoes phase shift. In addition, when the polarity of the displacement is reversed as illustrated in FIG. 19, the temporal change information analysis unit 8 determines that there is a separation in a portion between them. The temporal change information analysis unit 8 inputs the above-described time frequency distribution calculation result and defect determination result to the abnormality map creation unit 9.

In Step S11, the abnormality map creation unit 9 creates an abnormality map (x, y) based on the information input in the above-steps. The result sent from the two-dimensional spatial distribution information analysis unit 7 and the temporal change information analysis unit 8 is a group of data related to the point (x, y) on the X-Y coordinates. The structure status of these pieces of data is determined by the two-dimensional spatial distribution information analysis unit 7 and the temporal change information analysis unit 8 in the abnormality determination unit 6.

These determinations were performed on the displacement amount or the displacement distribution diagram in X-direction, the displacement amount or the displacement distribution diagram in Y-direction, the differential displacement amount or differential displacement distribution diagram, or the time response for the displacement or the differential displacement. Therefore, even when there is any lack of data, for example because of being unable to make a determination in the displacement amount in Y-direction, the abnormality map creation unit 9 can still decide the status of the corresponding portion in the X-Y coordinates, due to determination made for the displacement amount in X-direction and the differential displacement amount, and can create an abnormality map (x, y) based on this decision.

In the defect status determination, when there is any discrepancy in determination among X-direction displacement, Y-direction displacement, and differential displacement, the decision may be made by majority decision, or it is also possible to decide on the item having the greatest difference from the threshold value being the determination reference.

In addition, the abnormality map creation unit 9 may represent the degree of the defect based on various types of numerical value information described above. For example, it is possible to represent the width or depth of the crack, the size of the separation, or the size or depth from a surface of the internal cavity.

It is also possible to make the abnormality map creation unit 9 perform determination of the defect status of the structure while creating the abnormality map (x, y), which is performed by the two-dimensional spatial distribution information analysis unit 7 and the temporal change information analysis unit 8 in the abnormality determination unit 6. That is, analysis data may be obtained from the two-dimensional spatial distribution information analysis unit 7 and the temporal change information analysis unit 8, and the determination of the defect status based on that analysis data may be performed by the abnormality map creation unit 9.

In addition, the output of the result from the abnormality map creation unit 9 may be information in the form in which a person can directly view on a display device, or information in the form in which a machine can read.

In the present example embodiment, the lens focal distance of the image-capturing unit 11 may be 50 mm, and the pixel pitch may be 5 μm, so as to be able to obtain a pixel resolution of 500 μm at an image-capturing distance of 5 m. The image-capturing element of the image-capturing unit 11 may be monochroic, and has 2000 pixels horizontally and 2000 pixels vertically, to enable image-capturing the range of 1 m×1 m at an image-capturing distance of 5 m. The frame rate of the image-capturing element may be 60 Hz.

In addition, the sub-pixel displacement estimation by means of quadratic curve interpolation is adopted in the image correlation in the displacement calculation unit 2, so as to realize displacement estimation up to ¹/₁₀₀ pixels, and to obtain the displacement resolution of 5 μm displacement. The sub-pixel displacement estimation in image estimation may adopt the various methods as described below. In addition, in displacement differential, a smoothing filter may be used to reduce the noise when performing the differential operation.

Interpolation using quadratic curve, conformal straight line, or the like may be used for the sub-pixel displacement estimation. In addition, for the image correlation operation, various methods such as SAD (Sum of Absolute Difference) method, or SSD (Sum of Squared Difference) method, NCC (Normalized Cross Correlation) method, and ZNCC (Zero-mean Normalized Cross Correlation) method may be used. It is also possible to use any combination between these methods and the above-described sub-pixel displacement estimation method.

The lens focal distance of the image-capturing unit 11, and the pixel pitch, the pixel number, and the frame rate of the image-capturing element may be changed, depending on the object to be measured, where necessary.

In the present example embodiment, the beam-like structure may correspond to a bridge, and the loading may correspond to a traveling vehicle. In the above description, loading was explained to be applied on the beam-like structure. However, even when the loading moves on the bridge just as the traveling vehicle, a crack, an internal cavity, and a separation can be equally detected. In addition, the present example embodiment can be applied to any structure having a different material, size, or form, and to any loading method different from the method to apply loading on the structure, for example a loading method such as hanging the loading, as long as the structure can behave just as in the above description from the viewpoint of material mechanics.

In addition, not limited to time-series images, an array laser Doppler sensor, an array strain gauge, an array oscillation sensor, and an array acceleration sensor or the like may be used, as long as it can measure the time-series signals of a spatial two-dimensional distribution of the surface displacement of a structure. The spatial two-dimensional time-series signals obtained from these array sensors may be treated as image information.

In the present example embodiment, it is possible to obtain distance information or tilt information for calculating the out-of-plane displacement due to movement of a structure surface in the normal direction, from the images obtained by image-capturing the structure surface before and after loading application. In principle, it is possible to obtain the moving amount of a structure surface in the normal direction, by measuring the amount of deflection attributed to the loading, from the direction of the side of the structure. However, when for example the structure is a bridge or the like, from an operational point of view, it is extremely difficult to measure the bridge from its side, and therefore the measurement accuracy thereof is degraded. The present example embodiment can resolve this operational difficulty, and therefore can amend the displacement of the images of the structure surface with high accuracy. In addition, in the present example embodiment, it is not necessary to provide such devices or facilities to measure the amount of deflection from the direction of the side, which helps restrain the cost increase.

As described so far, according to the present example embodiments, it is possible to detect with favorable accuracy any defect of a structure, such as cracks, separations, or internal cavities, remotely without contact, while restraining costs.

The present invention is not limited to the above-described example embodiments, and can be modified in various ways within the scope of the invention described in the claims, and these modifications are also included in the scope of the present invention.

Furthermore, a part of all of the above-described example embodiments can also be described as, but not limited to, the following Supplementary notes.

(Supplementary Note 1)
A status determination device comprising:
a displacement calculation unit that, from time-series images of a structure surface before and after loading application, calculates a two-dimensional spatial distribution of a displacement of the time-series images;
a correction amount calculation unit that calculates a correction amount based on a moving amount of the structure surface in a normal direction due to the loading application, from the two-dimensional spatial distribution of the displacement of the time-series images;
a displacement correction unit that extracts a two-dimensional spatial distribution of a displacement of the structure surface, by subtracting the correction amount from the two-dimensional spatial distribution of the displacement of the time-series images; and
an abnormality determination unit that identifies a defect of the structure, based on comparison between the two-dimensional spatial distribution of the displacement of the structure surface and a prepared spatial distribution of a displacement having been prepared in advance.

(Supplementary Note 2)
The status determination device according to Supplementary note 1, wherein
the correction amount calculation unit estimates a tilt angle of the structure from the time-series images, and calculates the correction amount based on the moving amount corrected using the tilt angle.

(Supplementary Note 3)
The status determination device according to Supplementary note 1 or 2, comprising:
a differential displacement calculation unit that calculates a two-dimensional differential spatial distribution from the two-dimensional spatial distribution of the displacement of the structure surface, wherein
the abnormality determination unit identifies a defect of the structure, based on comparison between the two-dimensional differential spatial distribution and a differential spatial distribution of a differential displacement having been prepared in advance.

(Supplementary Note 4)
The status determination device according to any one of Supplementary notes 1 to 3, wherein
the abnormality determination unit identifies a defect of the structure, based on a temporal change of the two-dimensional spatial distribution of the displacement of the structure surface.

(Supplementary Note 5)
The status determination device according to Supplementary note 3 or 4, wherein
the abnormality determination unit identifies a defect of the structure, based on a temporal change of the two-dimensional differential spatial distribution.

(Supplementary Note 6)
The status determination device according to any one of Supplementary notes 1 to 5, wherein
the abnormality determination unit identifies a defect of the structure, based on comparison between a displacement amount of the displacement of the structure surface and a threshold value having been prepared in advance.

(Supplementary Note 7)
The status determination device according to any one of Supplementary notes 3 to 6, wherein
the abnormality determination unit identifies a defect of the structure, based on comparison between a differential displacement amount of the displacement of the structure surface and a threshold value having been prepared in advance.

(Supplementary Note 8)
The status determination device according to any one of Supplementary notes 1 to 7, comprising:
an abnormality map creation unit that creates an abnormality map that represents a location and a type of the defect, based on a determination result of the abnormality determination unit.

(Supplementary Note 9)
The status determination device according to any one of Supplementary notes 1 to 8, wherein
the type of the defect includes a crack, a separation, and an internal cavity.

(Supplementary Note 10)
The status determination device according to Supplementary note 9, wherein
the prepared spatial distribution of the displacement and the prepared differential spatial distribution of the differential displacement are based on information of the crack, the separation, and the internal cavity.

(Supplementary Note 11)

The status determination device according to any one of Supplementary notes 1 to 10, wherein
the two-dimensional spatial distribution includes a distribution of an X-direction displacement of the displacement on an X-Y plane and a distribution of a Y-direction displacement of the displacement on the X-Y plane.

(Supplementary Note 12)

A status determination system comprising:
a status determination device that includes: a displacement calculation unit that, from time-series images of a structure surface before and after loading application, calculates a two-dimensional spatial distribution of a displacement of the time-series images; a correction amount calculation unit that calculates a correction amount based on a moving amount of the structure surface in a normal direction due to the loading application, from the two-dimensional spatial distribution of the displacement of the time-series images; a displacement correction unit that extracts a two-dimensional spatial distribution of a displacement of the structure surface, by subtracting the correction amount from the two-dimensional spatial distribution of the displacement of the time-series images; and an abnormality determination unit that identifies a defect of the structure, based on comparison between the two-dimensional spatial distribution of the displacement of the structure surface and a spatial distribution of a displacement having been prepared in advance; and
an image-capturing unit that captures the time-series images and provides the status determination device with the time-series images.

(Supplementary Note 13)

The status determination system according to Supplementary note 12, wherein
the correction amount calculation unit estimates a tilt angle of the structure from the time-series images, and calculates the correction amount based on the moving amount corrected using the tilt angle.

(Supplementary Note 14)

The status determination system according to Supplementary note 12 or 13, comprising:
a differential displacement calculation unit that calculates a two-dimensional differential spatial distribution from the two-dimensional spatial distribution of the displacement of the structure surface, wherein
the abnormality determination unit identifies a defect of the structure, based on comparison between the two-dimensional differential spatial distribution and a differential spatial distribution of a differential displacement having been prepared in advance.

(Supplementary Note 15)

The status determination system according to any one of Supplementary notes 12 to 14, wherein
the abnormality determination unit identifies a defect of the structure, based on a temporal change of the two-dimensional spatial distribution of the displacement of the structure surface.

(Supplementary Note 16)

The status determination system according to Supplementary note 14 or 15, wherein
the abnormality determination unit identifies a defect of the structure, based on a temporal change of the two-dimensional differential spatial distribution.

(Supplementary Note 17)

The status determination system according to any one of Supplementary notes 12 to 16, wherein
the abnormality determination unit identifies a defect of the structure, based on comparison between a displacement amount of the displacement of the structure surface and a threshold value having been prepared in advance.

(Supplementary Note 18)

The status determination system according to any one of Supplementary notes 14 to 17, wherein
the abnormality determination unit identifies a defect of the structure, based on comparison between a differential displacement amount of the displacement of the structure surface and a threshold value having been prepared in advance.

(Supplementary Note 19)

The status determination system according to any one of Supplementary notes 12 to 18, comprising:
an abnormality map creation unit that creates an abnormality map that represents a location and a type of the defect, based on a determination result of the abnormality determination unit.

(Supplementary Note 20)

The status determination system according to any one of Supplementary notes 12 to 19, wherein
the type of the defect includes a crack, a separation, and an internal cavity.

(Supplementary Note 21)

The status determination system according to Supplementary note 20, wherein
the prepared spatial distribution of the displacement and the prepared differential spatial distribution of the differential displacement are based on information of the crack, the separation, and the internal cavity.

(Supplementary Note 22)

The status determination system according to any one of Supplementary notes 12 to 21, wherein
the two-dimensional spatial distribution includes a distribution of an X-direction displacement of the displacement on an X-Y plane and a distribution of a Y-direction displacement of the displacement on the X-Y plane.

(Supplementary Note 23)

A status determination method comprising:
calculating, from time-series images of a structure surface before and after loading application, a two-dimensional spatial distribution of a displacement of the time-series images;
calculating a correction amount based on a moving amount of the structure surface in a normal direction due to the loading application, from the two-dimensional spatial distribution of the displacement of the time-series images;
extracting a two-dimensional spatial distribution of a displacement of the structure surface, by subtracting the correction amount from the two-dimensional spatial distribution of the displacement of the time-series images; and
identifying a defect of the structure, based on comparison between the two-dimensional spatial distribution of the displacement of the structure surface and a spatial distribution of a displacement having been prepared in advance.

(Supplementary Note 24)

The status determination method according to Supplementary note 23, wherein
a tilt angle of the structure is estimated from the time-series images, and the correction amount is calculated based on the moving amount corrected using the tilt angle.

(Supplementary Note 25)

The status determination method according to Supplementary note 23 or 24, comprising:

calculating a two-dimensional differential spatial distribution from the two-dimensional spatial distribution of the displacement of the structure surface, wherein a defect of the structure is identified, based on comparison between the two-dimensional differential spatial distribution and a differential spatial distribution of a differential displacement having been prepared in advance.

(Supplementary Note 26)

The status determination method according to any one of Supplementary notes 23 to 25, wherein a defect of the structure is identified, based on a temporal change of the two-dimensional spatial distribution of the displacement of the structure surface.

(Supplementary Note 27)

The status determination method according to Supplementary note 25 or 26, wherein a defect of the structure is identified, based on a temporal change of the two-dimensional differential spatial distribution.

(Supplementary Note 28)

The status determination method according to any one of Supplementary notes 23 to 27, wherein a defect of the structure is identified, based on comparison between a displacement amount of the displacement of the structure surface and a threshold value having been prepared in advance.

(Supplementary Note 29)

The status determination method according to any one of Supplementary notes 25 to 28, wherein a defect of the structure is identified, based on comparison between a differential displacement amount of the displacement of the structure surface and a threshold value having been prepared in advance.

(Supplementary Note 30)

The status determination method according to any one of Supplementary notes 23 to 29, comprising:

creating an abnormality map that represents a location and a type of the defect, based on the identification result.

(Supplementary Note 31)

The status determination method according to any one of Supplementary notes 23 to 30, wherein the type of the defect includes a crack, a separation, and an internal cavity.

(Supplementary Note 32)

The status determination method according to Supplementary note 31, wherein the prepared spatial distribution of the displacement and the prepared differential spatial distribution of the differential displacement are based on information of the crack, the separation, and the internal cavity.

(Supplementary Note 33)

The status determination method according to any one of Supplementary notes 23 to 32, wherein the two-dimensional spatial distribution includes a distribution of an X-direction displacement of the displacement on an X-Y plane and a distribution of a Y-direction displacement of the displacement on the X-Y plane.

This application is based upon and claims the benefit of priority from Japanese patent application No. 2015-057047, filed on Mar. 20, 2015, the disclosure of which is incorporated herein in its entirety by reference.

INDUSTRIAL APPLICABILITY

The present invention can be applied to devices and systems that detect such defects as a crack, a separation, and an internal cavity generated in a structure such as a tunnel and a bridge, by observing from a remote location.

REFERENCE SIGNS LIST 1, 100 status determination device
2 displacement calculation unit
3 correction amount calculation unit
4 displacement correction unit
5 differential displacement calculation unit
6 abnormality determination unit
7 two-dimensional spatial distribution information analysis unit
8 temporal change information analysis unit
9 abnormality map creation unit
10 status determination system
11 image-capturing unit
12 structure
13 defect

What is claimed is:

1. A status determination device comprising:
a displacement calculation circuit that, from time-series images of a structure surface before and after loading application, calculates a two-dimensional spatial distribution of a displacement of the time-series images;
a correction amount calculation circuit that calculates a correction amount based on a moving amount of the structure surface in a normal direction due to the loading application, from the two-dimensional spatial distribution of the displacement of the time-series images;
a displacement correction circuit that extracts a two-dimensional spatial distribution of a displacement of the structure surface, by subtracting the correction amount from the two-dimensional spatial distribution of the displacement of the time-series images; and
an abnormality determination circuit that identifies a defect of the structure, based on comparison between the two-dimensional spatial distribution of the displacement of the structure surface and a prepared spatial distribution of a displacement having been prepared in advance.

2. The determination device according to claim 1, wherein the correction amount calculation circuit estimates a tilt angle of the structure from the time-series images, and calculates the correction amount based on the moving amount corrected using the tilt angle.

3. The determination device according to claim 1, comprising:
a differential displacement calculation circuit that calculates a two-dimensional differential spatial distribution from the two-dimensional spatial distribution of the displacement of the structure surface, wherein
the abnormality determination circuit identifies a defect of the structure, based on comparison between the two-dimensional differential spatial distribution and a differential spatial distribution of a differential displacement having been prepared in advance.

4. The determination device according to claim 1, wherein the abnormality determination circuit identifies a defect of the structure, based on a temporal change of the two-dimensional spatial distribution of the displacement of the structure surface.

5. The determination device according to claim 3, wherein the abnormality determination circuit identifies a defect of the structure, based on a temporal change of the two-dimensional differential spatial distribution.

6. The determination device according to claim 1, wherein the abnormality determination circuit identifies a defect of the structure, based on comparison between a displacement amount of the displacement of the structure surface and a threshold value having been prepared in advance.

7. The determination device according to claim 3, wherein the abnormality determination circuit identifies a defect of the structure, based on comparison between a differential displacement amount of the displacement of the structure surface and a threshold value having been prepared in advance.

8. The determination device according to claim 1, comprising:
an abnormality map creation circuit that creates an abnormality map that represents a location and a type of the defect, based on a determination result of the abnormality determination circuit.

9. A status determination system comprising:
a status determination device according to claim 1; and an image-capturing device that captures the time-series images and provides the status determination device with the time-series images.

10. A status determination method comprising:
calculating, from time-series images of a structure surface before and after loading application, a two-dimensional spatial distribution of a displacement of the time-series images;

calculating a correction amount based on a moving amount of the structure surface in a normal direction due to the loading application, from the two-dimensional spatial distribution of the displacement of the time-series images;

extracting a two-dimensional spatial distribution of a displacement of the structure surface, by subtracting the correction amount from the two-dimensional spatial distribution of the displacement of the time-series images; and identifying a defect of the structure, based on comparison between the two-dimensional spatial distribution of the displacement of the structure surface and a spatial distribution of a displacement having been prepared in advance.

* * * * *